(12) United States Patent
Hairrell et al.

(10) Patent No.: US 12,075,992 B1
(45) Date of Patent: Sep. 3, 2024

(54) FORCE TRANSFER MECHANISM

(71) Applicant: Auris Health, Inc., Redwood City, CA (US)

(72) Inventors: Adrian Tyler Hairrell, San Francisco, CA (US); Andre J. Castillo, Redwood City, CA (US); Akira Bryan Ueda, San Francisco, CA (US); Aadel Al-Jadda, San Carlos, CA (US)

(73) Assignee: Auris Health, Inc., Redwood City, CA (US)

( * ) Notice: Subject to any disclaimer, the term of this patent is extended or adjusted under 35 U.S.C. 154(b) by 741 days.

(21) Appl. No.: 17/134,175

(22) Filed: Dec. 25, 2020

Related U.S. Application Data

(60) Provisional application No. 62/955,996, filed on Dec. 31, 2019.

(51) Int. Cl.
| | |
|---|---|
| G05B 19/19 | (2006.01) |
| A61B 17/00 | (2006.01) |
| A61B 34/00 | (2016.01) |
| A61B 34/30 | (2016.01) |
| A61B 34/37 | (2016.01) |

(52) U.S. Cl.
CPC ............. *A61B 17/00* (2013.01); *A61B 34/30* (2016.02); *A61B 34/70* (2016.02); *A61B 2017/00199* (2013.01); *A61B 2017/00398* (2013.01); *A61B 2017/00486* (2013.01); *A61B 2017/00725* (2013.01); *A61B 34/37* (2016.02); *A61B 34/71* (2016.02); *G05B 2219/45083* (2013.01); *Y10S 901/08* (2013.01)

(58) Field of Classification Search
CPC .......... G05B 2219/45083; A61B 17/00; A61B 34/70; A61B 2017/00398; A61B 34/30; A61B 2017/00486; Y10S 901/08
See application file for complete search history.

(56) References Cited

U.S. PATENT DOCUMENTS

| | | | |
|---|---|---|---|
| 9,687,312 B2 | 6/2017 | Dachs, II | |
| 10,045,828 B2 | 8/2018 | Dachs, II | |
| 10,537,400 B2 | 1/2020 | Dachs, II | |
| 10,595,836 B2 | 3/2020 | Smaby | |
| 11,045,274 B2 | 6/2021 | Dachs, II | |
| 2008/0140088 A1 | 6/2008 | Orban, III | |
| 2022/0104901 A1* | 4/2022 | Lawrie | ............... A61B 17/1659 |

\* cited by examiner

*Primary Examiner* — Karen Masih
(74) *Attorney, Agent, or Firm* — Frost Brown Todd LLP

(57) ABSTRACT

The systems and devices disclosed herein can include a force transfer mechanism that permits force transfer between an instrument device manipulator and a tool coupled to the instrument device manipulator. The force transfer mechanism can include a first alignment member and a second alignment member. The first alignment member can have a disengaged position in which the first alignment member is out of engagement with the second alignment member, thereby reducing or preventing engagement between an instrument device manipulator base driveshaft and a tool driveshaft and permitting rotation of the base driveshaft relative to the tool driveshaft. When in an engaged position, the second alignment member can permit engagement between the base driveshaft to the tool driveshaft and transfer of rotary motion from the base driveshaft to the tool driveshaft. Additionally, the present disclosure also relates to methods of preparing and using a medical robotic system.

11 Claims, 14 Drawing Sheets

FORCE TRANSFER MECHANISM

CROSS REFERENCE TO RELATED APPLICATIONS

This application claims the benefit of priority to U.S. Provisional Application No. 62/955,996, filed on Dec. 31, 2019, the disclosure of which is incorporated herein by reference in its entirety for all purposes.

TECHNICAL FIELD

Systems, methods and devices disclosed herein are relates to medical robotic systems, and more particularly, to a force transfer mechanism for a medical robot.

BACKGROUND

Medical robots are increasingly being used to perform medical procedures such as endoscopy or laparoscopy because of the ability of these robots to manipulate tools in a way that humans traditionally could, with added advantages. For example, endoscopic or laparoscopic tools attached to medical robots can reduce the ergonomic load on the physician who can perform the procedures by manipulating the tools by commanding the robot from a comfortable position away from the site of the procedure. Additionally, because such tools can be constructed to enter and articulate into small spaces, the size of incision needed to perform the procedure can also be reduced, or the tool may enter the patient through a natural orifice, thereby reducing recovery time.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1:
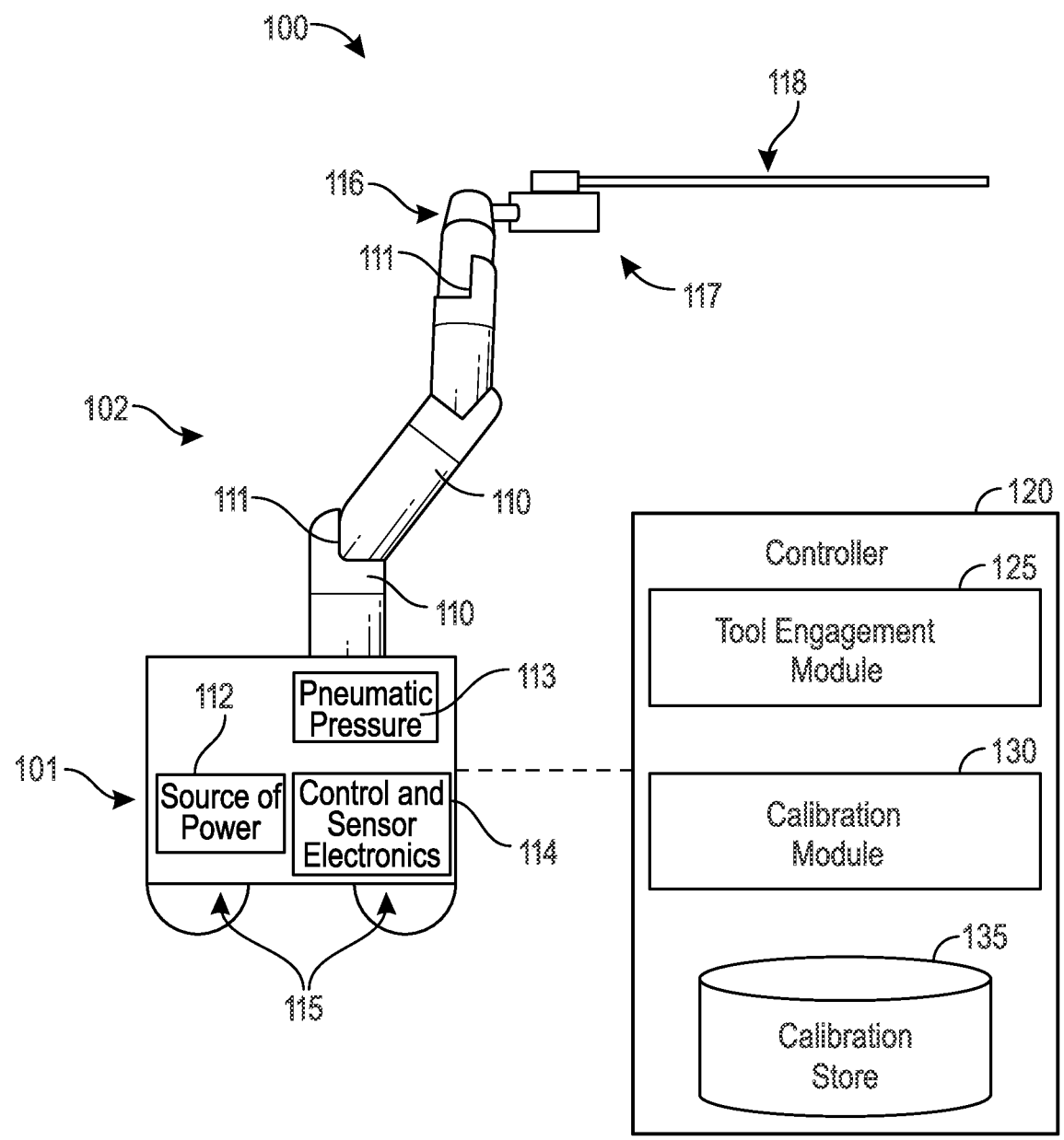
FIG. 1 illustrates a medical robotic system, according to some embodiments of the present disclosure.

Disclosed herein is a medical robotic system including one or more robotic arms, each of which can be coupled to a robotic tool. The robotic tools, upon coupling to the robotic arms, can be manipulated by a user, such as a physician, using a console from an ergonomic position for performing the medical procedures. Such a medical robotic system can provide an improvement in physician comfort, thereby enabling the physician to perform more complex tasks and for a longer period of time. As a result patient outcomes are improved. Additionally, such medical robotic systems enable minimally invasive procedures, thereby reducing recovery time.

According to some embodiments, a robotic arm of a medical robot is connected to an instrument device manipulator (IDM). The robotic arm can move the IDM to any position within a defined work space. Robotic tools such as a steerable catheter for endoscopic applications or any of a variety of laparoscopic tools can be connected to and manipulated by the IDM by activating control tools such as, for example, pull wires to steer a catheter or operate laparoscopic tools. Additionally, the IDM may be electrically and/or optically coupled to the tool to provide power, light, or control signals, and may receive data from the tool such as a video stream from a camera on the tool.

A force transfer mechanism for transferring force (or torque) from the IDM to the tool can include drive shafts on the IDM that couple with drive couplers on the tool. For reducing or preventing relative motion between the tool and the IDM once the tool is coupled to the IDM so as to transfer the force without latency, the drive shafts and the drive couplers may be aligned when coupling the tool. However, setup for a procedure may be cumbersome, and when performing the procedure, a user of the robotic system may not be able to divert his or her attention to ensure proper alignment between the tool and the IDM while he or she is focused on the subject and the procedure itself. A force transfer mechanism including alignment features can facilitate alignment of the drive shafts of the IDM with the drive couplers of the tool.

A surgical robotic system described herein may include a base driveshaft that defines a first rotational axis and has a first member, and a tool having a tool driveshaft that defines a second rotational axis. The tool additionally may include an asymmetric engagement interface having a second member, the second member being offset from the second rotational axis. The base driveshaft is engageable with the tool driveshaft upon alignment of the rotational positions of the base driveshaft and the tool driveshaft, thereby permitting engagement between the base driveshaft and the tool driveshaft for transferring rotary motion to the tool driveshaft.

A robotic tool that can be coupled to a medical robot disclosed herein is also described. The robotic tool may include a tool driveshaft having a rotational position that is alignable with a rotational position of a base driveshaft of an instrument device manipulator (IDM) of a medical robot, and a fixed alignment member is configured to engage to a moveable alignment member of the IDM when the rotational positions of the base driveshaft and the tool driveshaft are aligned. Transfer of motion between the base driveshaft and the tool driveshaft is permitted when the fixed alignment member is engaged with the moveable alignment member.

In some embodiments, a robotic tool may include a tool driveshaft and a moveable alignment member. The tool driveshaft has a rotational position alignable with a rotational position of a base driveshaft of an IDM having a fixed alignment member. The moveable alignment member has a disengaged position in which the moveable alignment member is recessed and out of engagement with the fixed alignment member when the rotational positions of the base driveshaft and the tool driveshaft are not aligned. In the disengaged position, the transfer of motion between the base driveshaft and the tool driveshaft is reduced or prevented. The moveable alignment member has an engaged position in which the moveable alignment member extends into engagement with the fixed alignment member when the rotational positions of the base driveshaft and the tool driveshaft are aligned. In the engaged position, transfer of motion between the base driveshaft and the tool driveshaft is permitted.

The various engagement mechanisms for engaging a robotic medical tool with a medical robotic arm disclosed herein can enable non-visual alignment of the medical tool with the IDM of the robotic arm. Advantageously, the inventive engagement mechanisms between the medical tool and the robotic arm disclosed herein also reduce or prevent relative rotational motion between the base driveshaft of the IDM and the driveshaft of the tool, thereby reducing latency in transferring motion from the IDM to the tool. In addition, with appropriate calibration of the tool, the engagement mechanisms may enable determination of a "zero position" of the tool's effector when the tool is first coupled to the IDM. The determination of the "zero position" enhances safety of the procedure being performed using the tool by informing the user about the position of the tool's effector, thereby allowing the user to make appropriate initial movements without harming the subject.

These and other features will be described in more detail below with reference to the embodiments illustrated in the figures, which are intended to illustrate certain example features and aspects of the technology described herein. The illustrated embodiments are not intended to be limiting, and those of skill in the art, upon consideration of this disclosure, will appreciate that various modifications can be made which are within the scope of this disclosure.

A. Medical Robotic System

FIG. 1 illustrates a medical robotic system 100 in accordance with some embodiments of the present disclosure. The system 100 may include a base 101 coupled to one or more robotic arms 102. The base 101 can be positioned such that the robotic arm 102 has access to perform a medical procedure such as, for example, endoscopy, ureteroscope, or laparoscopy, on a patient, while a user such as a physician may control the system 100 from an ergonomic site. In some embodiments, the base 101 is optionally communicatively coupled to a command console located at the ergonomically comfortable site, using which the user can control the system 100.

In some embodiments, the base 101 may be coupled to an operating table or bed for supporting the patient. Though not shown in FIG. 1 for purposes of clarity, the base 101 additionally or optionally includes subsystems such as control electronics, pneumatics, power sources, optical sources, and the like. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 may include wheels 115 to transport the system 100. Mobility of the system 100 advantageously helps accommodate space constraints in an operating room as well as facilitates appropriate positioning and movement of medical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes multiple arm segments 110 coupled at joints 111, which provide the robotic arm 102 multiple degrees of freedom. For example, the multiple arm segments can provide seven degrees of freedom corresponding to seven arm segments. In some embodiments, the robotic arm 102 includes set up joints that use a combination of brakes and counter-balances to maintain a position of the robotic arm 102. The counter-balances may include gas springs or coil springs. The brakes, such as fail safe brakes, may include mechanical and/or electrical components. In some embodiments, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM may manipulate an ureteroscope, while a second type of IDM may manipulate a laparoscope. In some embodiments, the IDM 117 may manipulate medical tools such as, for example, an ureteroscope 118, using manipulation methods including direct drive, harmonic drive, geared drives, belts and pulleys, magnetic drives, or any combination thereof. In some embodiments, the MCI 116 may include connectors to transfer pneumatic pressure, electrical power, electrical signals, and optical signals from the robotic arm 102 to the IDM 117. The MCI 116 can be a set screw or base plate connector. The MCI 116 can be interchangeable based on the type of IDM 117 and can be customized for a certain type of surgical procedure.

The ureteroscope 118 is a tubular and flexible instrument that is inserted into the anatomy of a patient to capture images of the anatomy (e.g., body tissue). In some embodiments, the ureteroscope 118 may include one or more imaging devices (e.g., cameras or sensors) that capture the images. The imaging devices may include one or more optical components such as an optical fiber, fiber array, or lens. The optical components move along with the tip of the ureteroscope 118 such that movement of the tip of the ureteroscope 118 results in changes to the images captured by the imaging devices. It will be appreciated that while an ureteroscope is used as the primary example throughout, it is understood that the surgical robotic system 100 may be used with a variety of surgical instruments.

In some embodiments, robotic arms 102 of the system 100, and more particularly, the IDMs 117 of the corresponding robotic arms 102, manipulate the corresponding medical tools using elongate movement members. The elongate movement members may include pull-wires, also referred to as pull or push wires, cables, fibers, or flexible shafts. For example, the robotic arms 102 actuate multiple pull-wires coupled to the ureteroscope 118 to deflect the tip of the ureteroscope 118. The pull-wires may include both metallic and non-metallic materials such as stainless steel, Kevlar, tungsten, carbon fiber, and the like. In some embodiments, the ureteroscope 118 may exhibit nonlinear behavior in response to forces applied by the elongate movement members. The nonlinear behavior may be based on stiffness and compressibility of the ureteroscope 118, as well as variability in slack or stiffness between different elongate movement members.

The system 100 may also include a controller 120, for example, a computer processor. In some embodiments, the controller 120 may include a tool engagement module 125 and a calibration module 130. The tool engagement module 125, during coupling of the robotic tool 118 with the IDM 117, can manipulate base driveshafts of the IDM to appropriately align with tool driveshafts of the robotic tool 118 being coupled to the IDM 117, thereby permitting engagement of the robotic tool 118 with the IDM 117.

Once the tool 118 is coupled to the IDM, the calibration module 130 determines the rotational position of each of the base driveshafts at which the corresponding tool driveshaft aligns with it. The calibration module 130 then determines the rotational position of each of the tool driveshafts at the time of coupling. The rotational positions of the tool driveshafts provide information about the position of the effector of the robotic tool 118 at the time of coupling, referred to herein as the "zero-position."

Determining the "zero-position" of the effector of the robotic tool 118 allows the user to determine how to initially manipulate the effector. Thus, the information about the "zero-position" helps the user decrease the potential for wrong movements of the effectors and increasing safety of the procedure being performed.

Advantageously, knowing the "zero-position" also decreases the potential for damage to the tool itself. For example, knowing the "zero-position" enables the user to avoid movements that may increase tensile stress on the elongate members manipulating the effector of the tool 118 to increase beyond a certain threshold, such as yield stress or breaking stress. Similarly, the information about the "zero-position" may also reduce latency in movement of the effector by enabling the user to avoid movements that lead to a slack in the elongate members.

In some embodiments, the calibration module 130 can optionally characterize the nonlinear behavior of the identified tool 118 coupled to the IDM 117. In some embodiments, the characterization of the nonlinear behavior may be performed using a model with piecewise linear responses along with parameters such as, for example, slopes, hystereses, and dead zone values. The system 100 can more accurately control the robotic tool 118 by determining accurate values of the parameters. These and other parameters, as well as the "zero-position" information may then be stored at the calibration store 135.

In some embodiments, some or all functionality of the controller 120 is performed outside the system 100, for example, on another computer system or server communicatively coupled to the system 100.

B. Command Console

Figure 2:
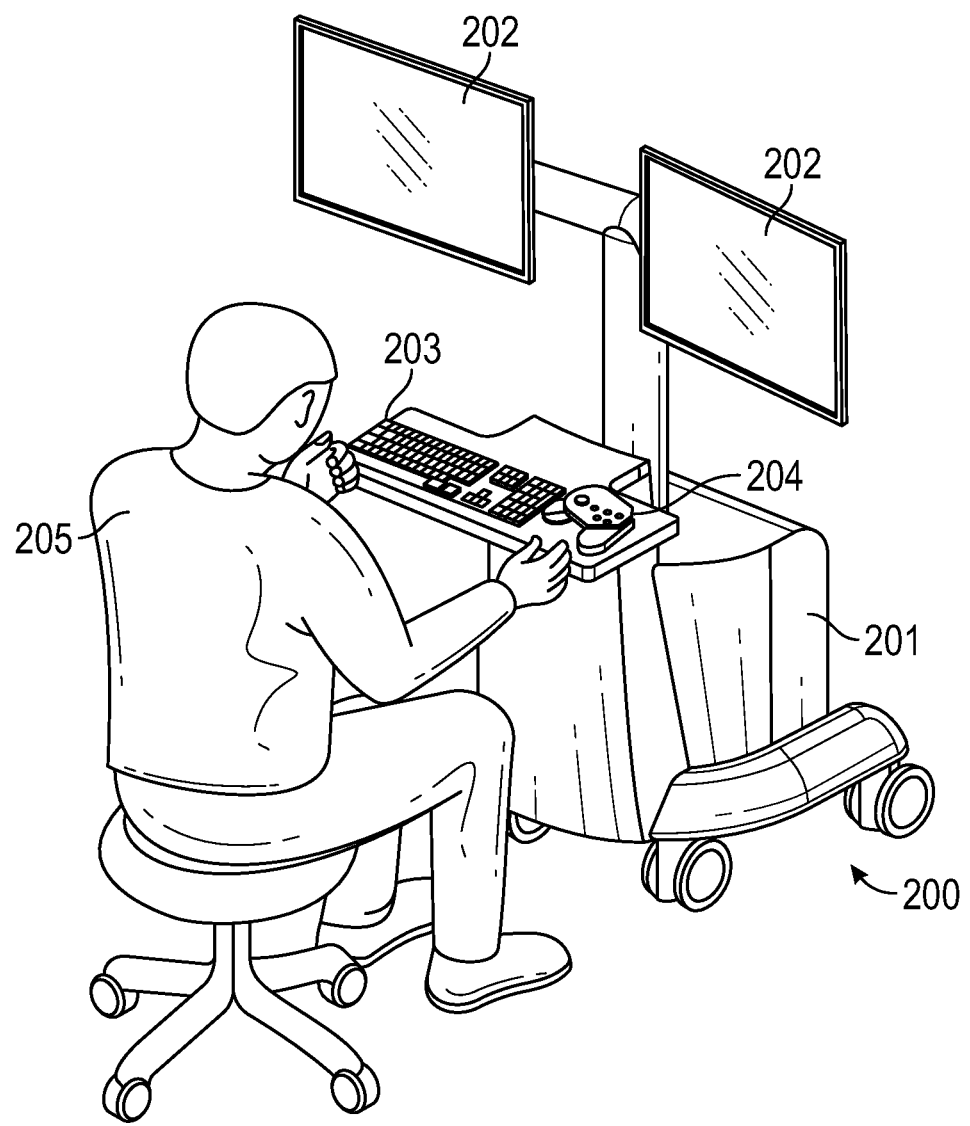
FIG. 2 illustrates a command console for a medical robotic system, according to some embodiments.

FIG. 2 illustrates a command console 200 for a medical robotic system 100 according to some embodiments of the present disclosure. The command console 200 includes a console base 201, display modules 202, and control modules. Examples of display modules include, but are not limited to, monitors. Examples of control modules include, but are not limited to, a keyboard 203 and joystick 204. In some embodiments, one or more of the command module 200 functionality may be integrated into a base 101 of the surgical robotic system 100 or another system communicatively coupled to the surgical robotic system 100. A user 205 may remotely control the system 100 from an ergonomic position using the command console 200.

The console base 201 may include a central processing unit, a memory unit, a data bus, and associated data communication ports that are responsible for interpreting and processing signals such as camera imagery and tracking sensor data. For example, the central processing unit may process signals and data from the tool 118 shown in FIG. 1. In some embodiments, both the console base 201 and the base 101 perform signal processing for load-balancing. The console base 201 may also process commands and instructions provided by the user 205 through the control modules. In addition to the keyboard 203 and joystick 204 shown in FIG. 2, the control modules may include other devices, for example, computer mice, track pads, trackballs, control pads, video game controllers, and sensors that capture hand gestures and finger gestures. Examples of sensors include, but are not limited to, motion sensors and cameras.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the system 100 using the integrated display modules 202 and control modules, in some embodiments.

C. Instrument Device Manipulator

Figure 3:
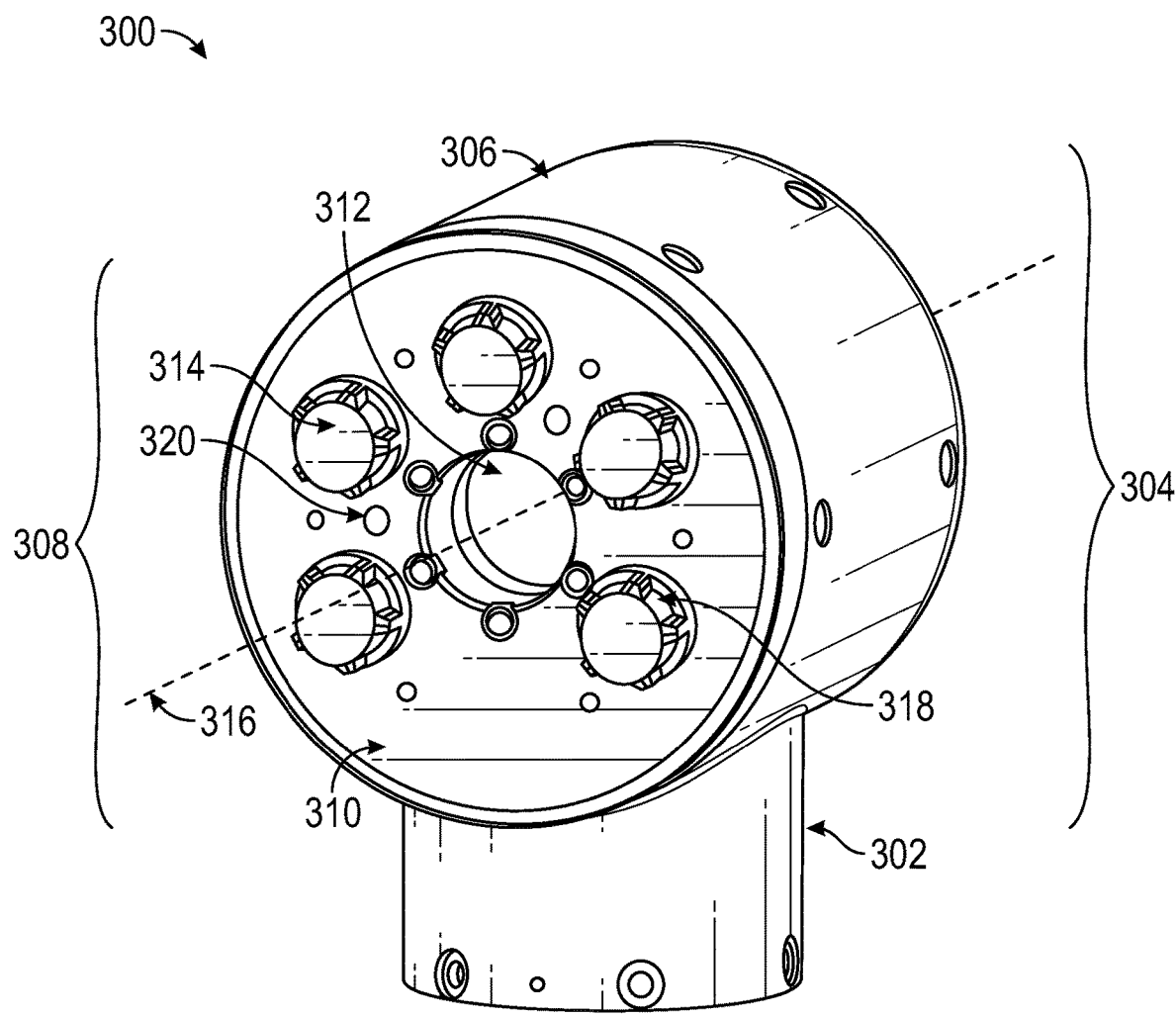
FIG. 3 illustrates a perspective view of an instrument device manipulator (IDM) for a medical robotic system, according to some embodiments.
Figure 4:
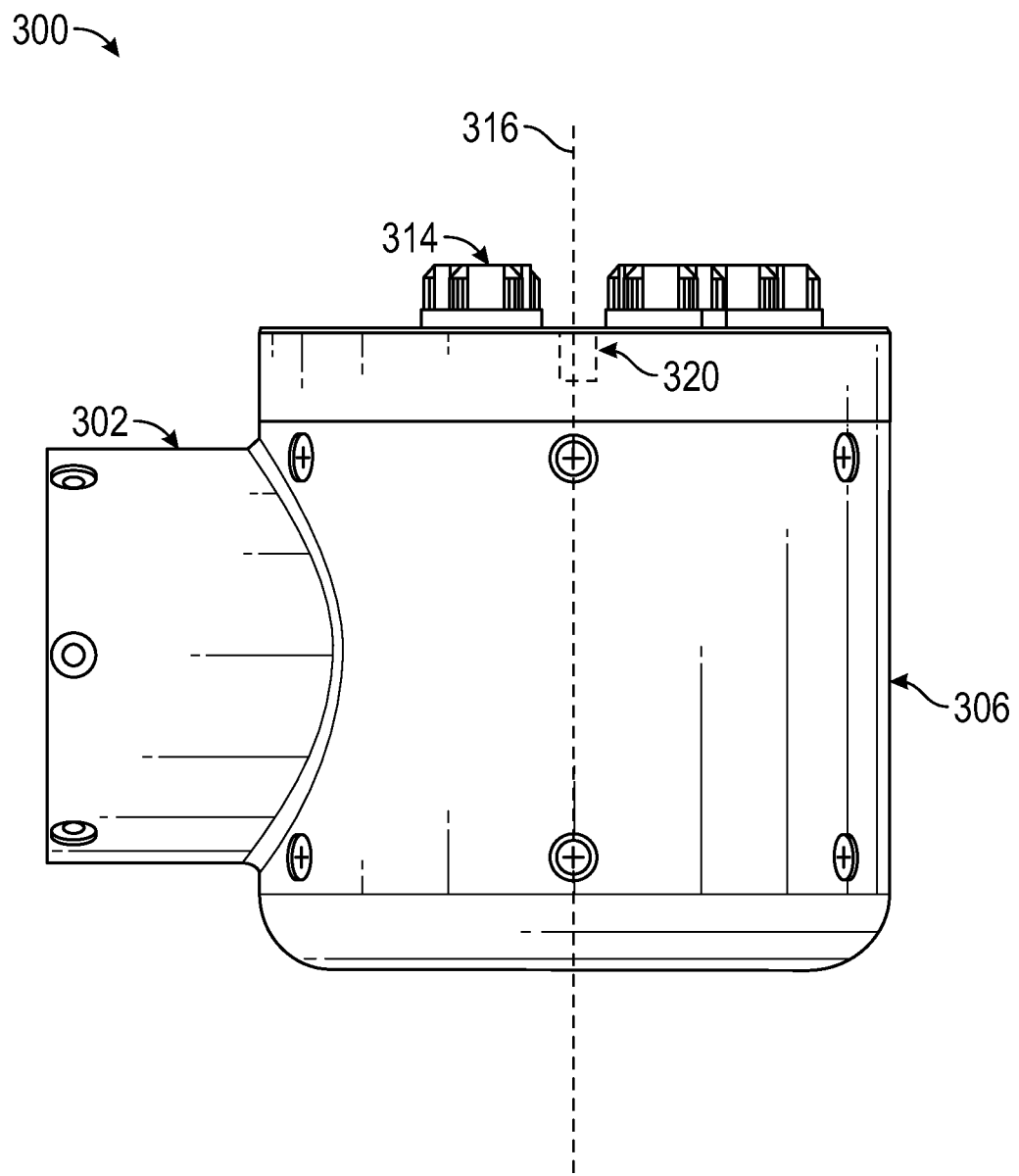
FIG. 4 is a side view of the IDM, according to some embodiments.

FIG. 3 illustrates a perspective view of an instrument device manipulator (IDM) 300 for a medical robotic system, and FIG. 4 is a side view of the IDM 300, according to some embodiments of the present disclosure. The IDM 300 is configured to attach a robotic tool such as the tool 118 to a robotic arm. In some embodiments, the IDM 300 is configured to attach to the robotic tool in a manner that allows the tool to be continuously rotated or "rolled" about an axis of the tool. The IDM 300 includes a base 302 and a tool holder assembly 304. The tool holder assembly 304 further includes an outer housing 306, a tool holder 308, an attachment interface 310, a plurality of torque couplers or base driveshafts 314, and optionally a passage 312. The IDM 300 may be used with a variety of medical tools (not shown in FIG. 3). The medical tools may include a housing and an elongated body. The medical tools may be used for procedures such as laparoscopy, endoscopy, or ureteroscopy. The medical tools may have articulable components, such as deflectable distal tips for steering, actuatable wrists, or other manipulatable components for interacting with target sites within a patient. For example, the actuatable wrists may be used for grasping, cutting or other operations. Other manipulatable components may include, but are not limited to, energy delivery devices, basketing tools, extendable needles, etc. Thus, the medical tools may have different end-effectors suitable for the corresponding procedure.

The base 302 removably or fixedly mounts the IDM 300 to a robotic arm of the system. In the embodiment of FIG. 3, the base 302 is fixedly attached to the outer housing 306 of the tool holder assembly 304. In some embodiments, the base 302 may be structured to include a platform which is adapted to rotatably receive the tool holder 308 on the face opposite from the attachment interface 310. The platform may optionally include an additional passage aligned with the passage 312 to receive the elongated body of the tool. In some embodiments, an additional elongated body of a second surgical tool is mounted coaxially with the first surgical tool.

The tool holder assembly 304 is configured to secure a tool to the IDM 300 and can be configured to rotate the tool relative to the base 302. In some embodiments, mechanical and electrical connections may be provided from the robotic arm to the base 302 and then to the tool holder assembly 304 to rotate the tool holder 308 relative to the outer housing 306. The connections facilitate manipulation and/or delivery of power and/or signals from the robotic arm to the tool holder 308 and ultimately to the tool. Signals may include signals for pneumatic pressure, electrical power, electrical signals, and/or optical signals.

In some embodiments, the outer housing 306 provides support for the tool holder assembly 304 with respect to the base 302. The outer housing 306 may be fixedly attached to the base 302 such that it remains stationary relative to the base 302, while allowing the tool holder 308 to rotate freely relative to the outer housing 306. In the embodiment of FIG. 3, the outer housing 306 is cylindrical in shape and fully circumscribes the surgical tool holder 308. The outer housing 306 may be composed of rigid materials (e.g., metals or hard plastics). It will be appreciated that the shape of the housing may vary.

The tool holder 308 functions to secure a tool to the IDM 300 via the attachment interface 310. The tool holder 308 is capable of rotating independent of the outer housing 306. In some embodiments, the tool holder 308 rotates about a rotational axis 316, which co-axially aligns with the elongated body of a tool such that the tool rotates with the tool holder 308.

The attachment interface 310 can define a face of the tool holder 308 that attaches to the tool. The attachment interface 310 may include a first portion of an attachment mechanism that reciprocally mates with a second portion of the attachment mechanism located on the tool. In some embodiments, the attachment interface 310 includes a plurality of torque couplers 314, also referred to herein as base driveshafts, that protrude outwards from the attachment interface 310. The torque couplers 314 may engage with respective instrument inputs, also referred to herein as tool driveshaft, on the tool. In some embodiments, a surgical drape, coupled to a sterile adapter, may be used to create a sterile boundary between the IDM 300 and the tool. In these embodiments, the sterile adapter may be positioned between the attachment interface 310 and the tool when the tool is secured to the IDM 300 such that the surgical drape separates the tool and the patient from the IDM 300 and the robotic system.

In some embodiments, the plurality of base driveshafts 314 are configured to engage and drive the components of the tool when the tool is secured to the tool holder 308. Each base driveshaft 314 is coupled to a respective tool driveshaft located on the tool. The plurality of base driveshafts 314 may also serve to maintain rotational alignment between the tool and the tool holder 308.

As illustrated in FIG. 3, each base driveshaft 314 is shaped as a cylindrical protrusion that protrudes outwards from the attachment interface 310. Notches 318 may be arranged along the outer surface area of the cylindrical protrusion. In some embodiments, the arrangement of the notches 318 creates a spline interface. The tool driveshafts of the tool are configured to have a complementary geometry to the base driveshafts 314 or couplers of the sterile adapter.

For example, while not shown in FIG. 3, the tool driveshafts of the tool or couplers of the sterile adapter may be cylindrical in shape and have a plurality of ridges that reciprocally mate with the plurality of notches 318 on each base driveshaft 314. In embodiments utilizing the sterile adapter, the couplers of the sterile adapter may mate with the tool driveshafts of the tool in a similar fashion. Thus, the base driveshafts 314 may engage with the tool driveshafts directly or via couplers in the sterile adapter. The notches 318 impart torque to the ridges when the base driveshaft is rotated. In some embodiments, the top face of the cylindrical protrusion may include the plurality of notches 318 configured to mate with a plurality of ridges in respective tool driveshafts or couplers of the sterile adapter. In this configuration, each base driveshaft 314 fully engages with its respective tool driveshaft or coupler.

Each base driveshaft 314 may be driven by a respective actuator that causes the base driveshaft to rotate in either direction. Thus, once engaged with tool driveshaft, each base driveshaft 314 is capable of transmitting power to tighten or loosen pull-wires within a tool, thereby manipulating a tool's end-effectors. In the embodiment of FIG. 3, the IDM 300 includes five base driveshafts 314, but the number may vary in other embodiments depending, for example, on the desired number of degrees of freedom for a tool's end-effectors or the construction of internal mechanisms of the tool.

Each base driveshaft 314 may be coupled to a spring that allows the base driveshaft 314 to translate in an axial direction. In some embodiments, the spring causes each base driveshaft to be biased to move axially outwards away from the attachment interface 310. In some embodiments, each base driveshaft 314 is capable of partially retracting into the tool holder 308. In some embodiments, each base driveshaft 314 is capable of fully retracting into the tool holder 308 such that the effective height of each base driveshaft 314 relative to the attachment interface 310 is zero.

In some embodiments, a surgical drape, coupled to a sterile adapter, may be used to create a sterile boundary between the IDM 300 and the tool. In these embodiments, the sterile adapter may be positioned between the attachment interface 310 and the tool when the tool is secured to the IDM 300, and the sterile adapter may be configured to transmit power from each base driveshaft 314 to the respective tool driveshaft.

In some embodiments, the sterile adapter may include an alignment interface that mates with the base driveshaft 314 on the IDM side, and with the tool driveshaft on the tool side. The spring-loaded base driveshaft 314 described herein facilitates alignment of the alignment interface of the sterile adapter with the base driveshaft when the sterile adapter is being coupled to the IDM 300. Each of the base driveshafts can be rotated independently in a retracted position to a rotational position where the corresponding base driveshaft can mate and engage with the alignment interface of the sterile adapter.

D. Sterile Adapter

Figure 5:
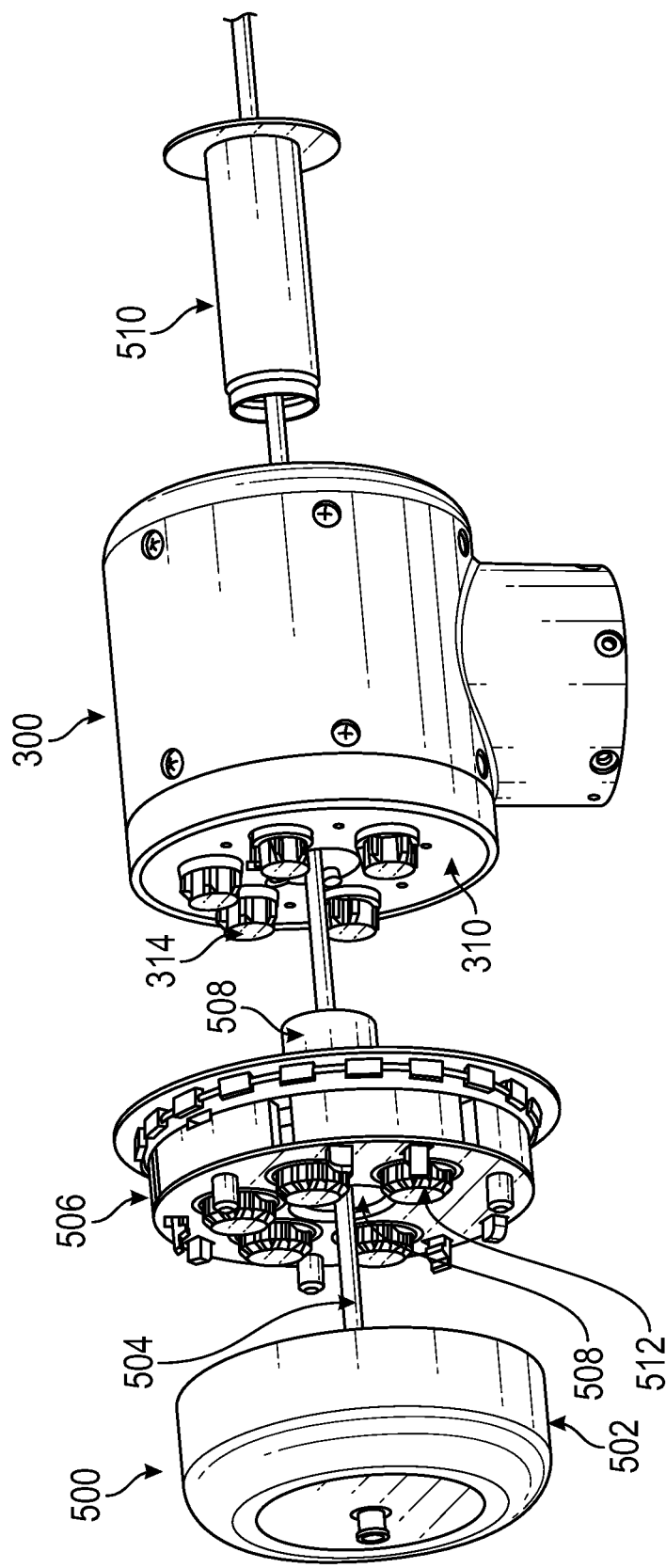
FIGS. 5 and 6 illustrate perspective exploded views of an example tool coupled to the IDM of FIG. 3, according to some embodiments.
Figure 6:
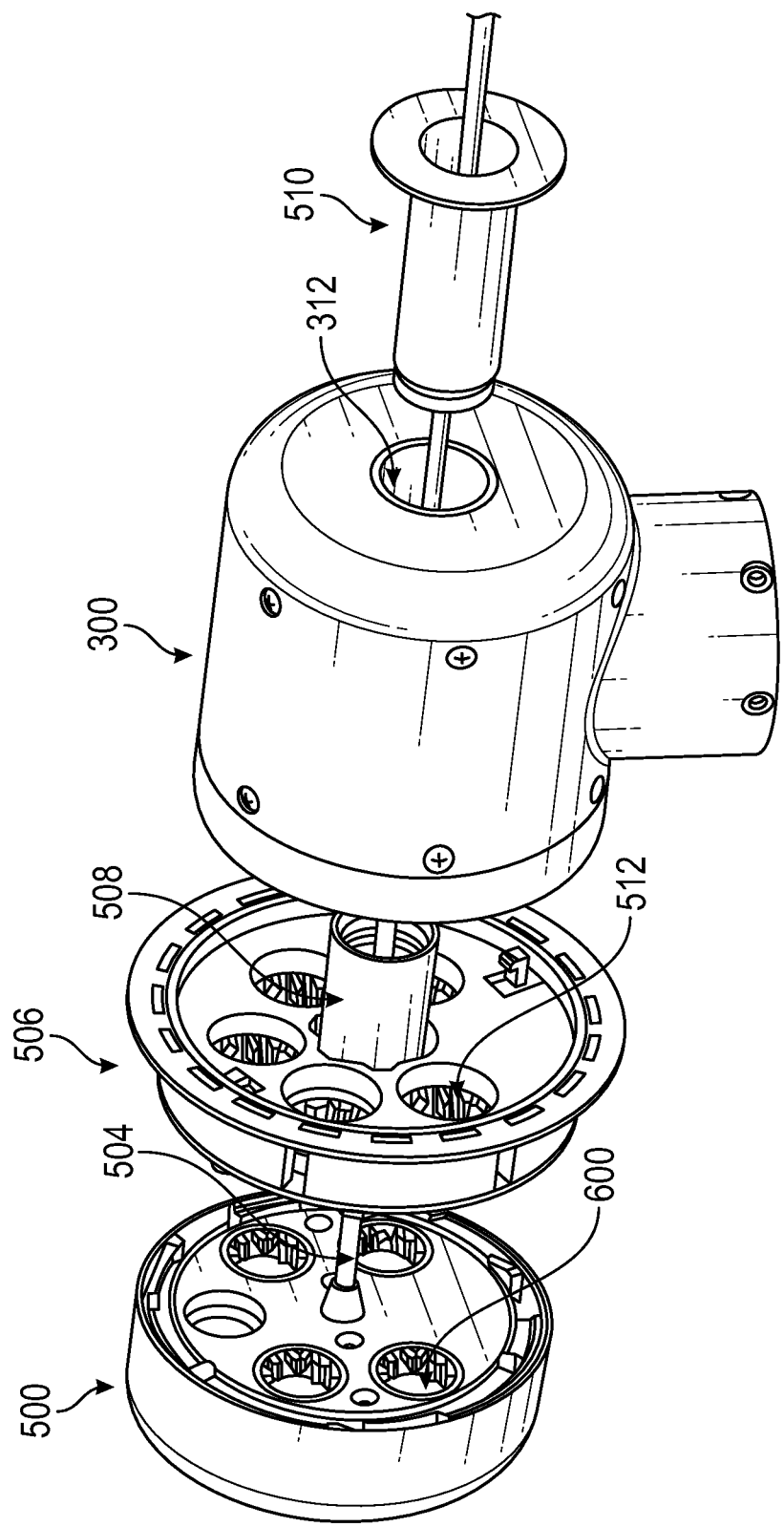

FIGS. 5-6 illustrate perspective exploded views of an example tool 500 coupled to the instrument device manipulator 300 of FIG. 3, according to some embodiments of the present disclosure. In some embodiments, the tool 500 includes a housing 502, an elongated body 504, and a plurality of instrument inputs 600. As described herein, the elongated body 504 may be a laparoscope, an ureteroscope, or other surgical instrument having end-effectors. As illustrated, the plurality of base driveshafts 314 protrude outwards from the attachment interface 310 to engage with the tool driveshafts 600 of the surgical tool. The structure of the tool driveshafts 600 can be seen in FIG. 6, wherein the tool driveshafts 600 have corresponding geometry to the base driveshafts 314.

During a medical procedure, in order to maintain a sterile boundary between the IDM 300 and the tool 500, a sterile adapter 506 may be coupled to the IDM 300 intermediate the tool 500 and the IDM 300. While not shown in FIGS. 5-6, in some embodiments, a sterile sheet may be connected to the sterile adapter 506, so as to drape around the IDM 300 to create the sterile boundary.

The sterile adapter 506 can create a sterile interface between the IDM 300 and the tool 500 when secured to the IDM 300. In the embodiment of FIGS. 5-6, the sterile adapter 506 has a disk-like geometry that covers the attachment interface 310 of the IDM 300. The sterile adapter 506 includes a central hole configured to receive the elongated body 504 of the surgical tool 500. In this configuration, the sterile adapter 506 is positioned between the attachment interface 310 and the tool 500 when the tool 500 is secured to the IDM 300. The arrangement creates a sterile boundary between the tool 500 and the IDM 300. The arrangement further allows the elongated body 504 to pass through the passage 312.

In some embodiments, the sterile adapter 506 may be capable of rotating with the tool holder 308, transmitting the rotational torque from the plurality of base driveshafts 314 to the tool 500, passing electrical signals between the IDM 300 and the tool 500, or some combination thereof.

Referring back to FIGS. 5-6, the sterile adapter 506 can include a first protrusion 508 and a second protrusion 510 to maintain a sterile boundary between the tool and the IDM within the passage 312. The first protrusion 508 and the second protrusion 510 are configured to pass through the passage 312 of the IDM 300 and mate with each other inside the passage 312. Each protrusion 508, 510 is structured to allow the elongated body 504 to pass through the protrusion and thus the passage 312. The connection of the first protrusion 508 and the second protrusion 510 creates the sterile boundary between the IDM 300 and the outside environment (i.e., an operating room).

It will be understood that while the Figures illustrate a certain geometry and configuration of the sterile adapter 506 and the IDM 300, other configurations and geometries are contemplated within the scope of the present disclosure. For example, the sterile adapter may have a square or a rectangular shape depending on the shape of the IDM and/or the tool. In some embodiments, the sterile adapter may not include the first and second protrusions or the IDM may not include the passage 312. For example, if the elongate body 504 of the tool extends transverse to the attachment interface 310 or does not extend through the IDM 300, the protrusions 508, 510 of the sterile adapter 506 and/or the passage 312 through the IDM 300 may be omitted.

In the embodiment illustrated in FIGS. 5-6, the sterile adapter 506 further includes a plurality of alignment members 512, also referred to herein as driveshaft coupler, or couplers. A first side of a coupler 512 is configured to engage with a respective base driveshaft 314 while a second side of a coupler 512 is configured to engage with a respective tool driveshaft 600.

Figure 7:
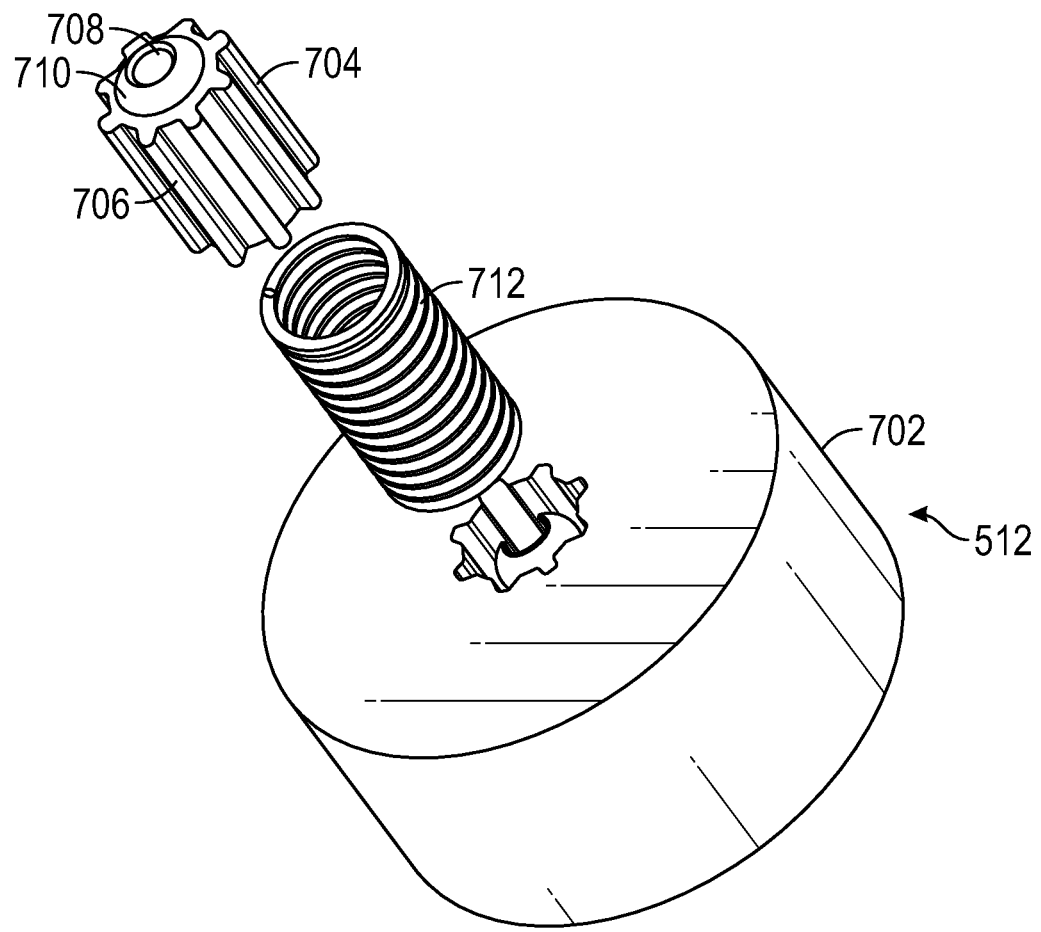
FIG. 7 illustrates an exploded view of an engagement mechanism between a driveshaft coupler of the sterile adapter and a tool, according to some embodiments.
Figure 8:
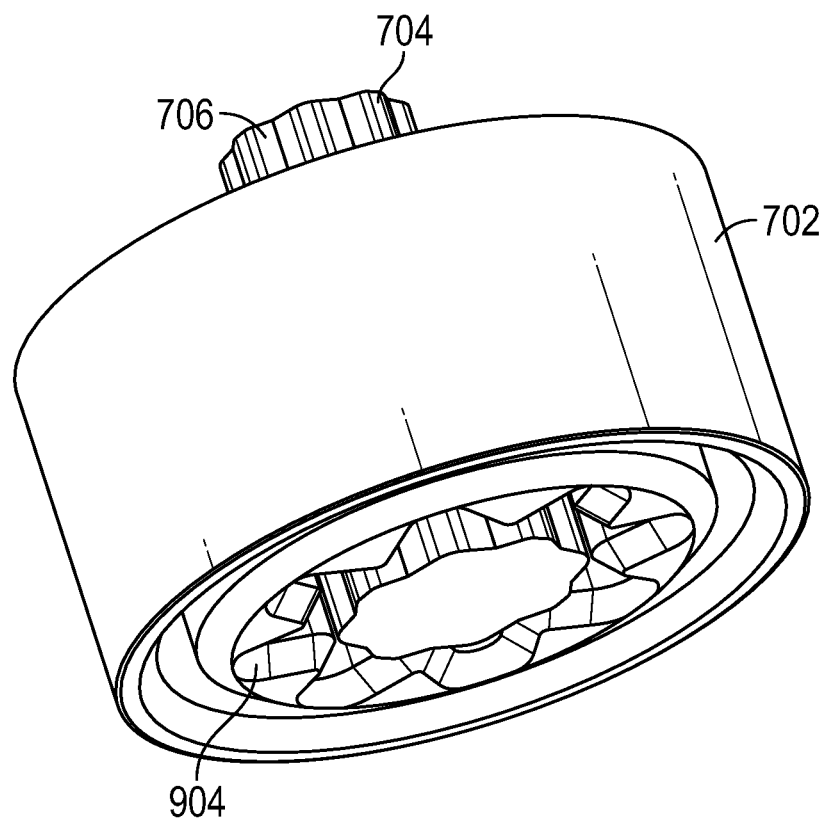
FIG. 8 illustrates a perspective view of an engagement mechanism between a driveshaft coupler of the sterile adapter and a tool, according to some embodiments.
Figure 9:
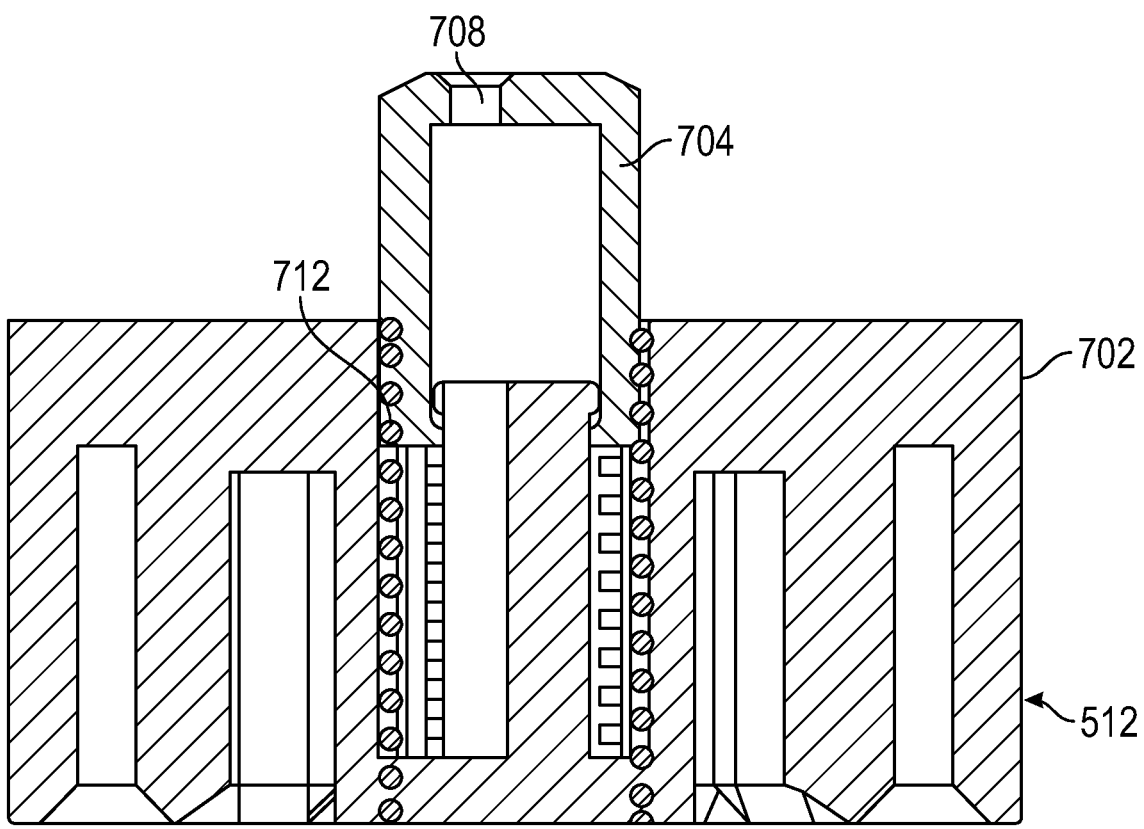
FIG. 9 illustrates a cross-section view of an engagement mechanism between a driveshaft coupler of the sterile adapter and a tool, according to some embodiments.

FIGS. 7-9 illustrate views of an engagement mechanism between a coupler 512 of the sterile adapter 506 and a tool, according to some embodiments of the present disclosure. In some embodiments, on the tool side, each coupler 512 has a base 702 and a moveable alignment member 704.

For example, in some embodiments, the moveable alignment member 704 is a structure that includes a cylindrical protrusion including a plurality of notches 706. The term "moveable alignment member," as used herein signifies that the alignment member is moveable relative to the driveshaft on which it is disposed. In the embodiment illustrated in FIGS. 7-8, the moveable alignment member 704 is moveable relative to the driveshaft coupler 512.

On the IDM side, the coupler 512 has slots 904 complementary to the notches of the corresponding IDM base driveshaft 314 to fully engage with the corresponding base driveshaft 314. Each coupler 512 is configured to rotate in a clockwise or counter-clockwise direction with the corresponding base driveshaft 314. This configuration allows each coupler 512 to transfer torque and rotary motion from a corresponding base driveshaft 314 of the IDM 300 to a corresponding tool driveshaft of the tool. The IDM 300 can, thus, control the end-effectors of the tool.

In some embodiments, the moveable alignment member 704 includes an engagement component 708 (such as a recess, a hole, a socket, a slit, or an aperture) which can be offset from the rotational axis of the coupler 512. The tool driveshaft may include a fixed alignment member having a shape corresponding to the aperture 708. As used herein, the term "fixed alignment member" signifies that the alignment member is fixed relative to the driveshaft on which it is disposed.

For example, in some embodiments, the fixed alignment member may be disposed on the tool driveshaft, and is, therefore, fixed relative to the tool driveshaft. For example, the fixed alignment member may not move relative to the tool driveshaft, but may move with the tool driveshaft. For example, the fixed alignment member may revolve about the rotational axis of the tool driveshaft when the tool driveshaft is rotated during operation of the robotic system.

Thus, when the rotational position of the coupler 512 and the rotational position of the tool driveshaft are aligned and the aperture 708 and the fixed alignment member of the tool driveshaft are aligned, the fixed alignment member can be received into the aperture 708.

In addition, the coupler 512 includes a biasing member, such as, for example a coil spring 712, configured to bias the moveable alignment member 704 into an extended position. In the extended position, the moveable alignment member 704 engages with the tool driveshaft. The spring 712 facilitates the moveable alignment member 704 to be moveable relative to the base 702 of the coupler 512 and into engagement with the fixed alignment member upon rotational alignment between the moveable and fixed alignment members.

When the rotational positions of the tool driveshaft and the coupler 512 are not aligned, the aperture 708 is not aligned with the fixed alignment member of the tool driveshaft. In such configuration, the fixed alignment member may push against a surface 710 of the moveable alignment member 704 to push the moveable alignment member 704 into a depressed or retracted position into the base 702, thereby compressing the spring 712.

When the rotational positions of the coupler 512 and the tool driveshaft are aligned, the moveable alignment member 704 is aligned with the fixed alignment member of the tool driveshaft. In such configuration, the fixed alignment member is received into the aperture 708. The force being exerted on the surface 710 of the moveable alignment member 704 is, therefore, removed. The compressed spring 712 then releases the stored energy, thereby urging the moveable alignment member 704 in an extended position where it engages with the tool driveshaft.

The position of the aperture 708 of the moveable alignment member 704 is designed to ensure alignment of the notches of the coupler 512 with corresponding structures in the tool driveshaft of the tool. Thus, the coupler 512 is fully engaged with the tool driveshaft when the moveable alignment member 704 is engaged with the fixed alignment member. Such complete engagement between the coupler 512 and the tool driveshaft causes the coupler 512 and tool driveshaft to rotate together when engaged, such that there is no relative rotational motion between the coupler 512 and the tool driveshaft when the coupler 512 and the tool driveshaft are engaged. For example, when the moveable alignment member 704 is engaged with the fixed alignment member (e.g., the aperture 708 can receive the fixed alignment member), motion or torque can be transferred between the coupler 512 and the tool driveshaft without latency.

It will be appreciated that the offset positioning of the aperture 708, and correspondingly of the fixed alignment member of the tool driveshaft, results in only one rotational position in which the coupler 512 and the tool driveshaft can engage. Such arrangement may be helpful in providing information about the exact rotational position of the end-effector of the tool at the time the tool is coupled with the robotic system, i.e., the "zero-position" of the end-effector. Advantageously, this information enables the user to determine an initial direction and magnitude by which to move the end-effector to get the end-effector into a desired position when performing a procedure.

Moreover, because the user may not necessarily know the position of the end-effector when the tool is coupled with the robotic system, moving the end-effectors immediately after the tool is coupled with the robotic system may result in undesirable positioning of the end-effector. Such "blind" movement can potentially cause risk to the subject on which the procedure is being performed. Thus, determining the "zero-position" of the end-effectors may improve safety of the procedure being performed.

While offset positioning of the aperture 708 and the fixed alignment member are shown in the figures, and described in detail herein, it will be understood that such offset arrangement is not the only way to ensure that the coupler 512 and the tool engage at only one rotational position. For example, in some embodiments, an aperture with a non-circular shape may be positioned along the rotational axis of the coupler 512 such that the corresponding fixed alignment member can engage with the aperture at a single rotational position. Examples of such apertures may include a T-shaped aperture, an I-shaped aperture with differently sized horizontal bars, an L-shaped aperture, or a slit positioned asymmetrically relative to the rotational axis of the coupler 512.

In some embodiments, the aperture may be shaped such that there are two rotational positions of engagement. For example, an aperture shaped like a rectangular slit and symmetrically positioned along the rotational axis of the coupler 512 may receive a correspondingly shaped fixed alignment member at two different rotational positions. Other shapes such as, for example, an equilateral triangle, square, a plus, a cross, a regular hexagon, or a pentalobe, of the aperture, allowing for more than two rotational positions of engagement between the tool and the coupler are also contemplated in the scope of the present disclosure.

Thus, while the embodiments illustrated in FIGS. 7-8 show a circular aperture 708 that can receive a cylindrical fixed alignment member, the aperture 708 may have the cross-sectional shape of a regular or irregular, polygon which may or may not be a convex polygon. Examples of shapes of the aperture include, but are not limited to, a slit (i.e., an elongate quadrangle), a triangle, a square, a hexagon, a pentagon, an I-shape, a cross, a plus, or a pentalobe. For example, the fixed alignment member may have any cross-sectional shape such as, for example, a triangle, quadrangle, pentagon, hexagon, pentalobe, I-shape, or cross shape.

It will be further appreciated that while the embodiments illustrated in FIGS. 7-8 show the coupler 512 including a cylindrical protrusion 704, the moveable alignment member may be a spline including an elongate body having any cross-sectional shape. Examples of the shapes of the coupler include, but are not limited to, a circle (e.g., the cylindrical protrusion 704), a quadrangle, a convex polygon, a non-convex polygon, or any combination thereof. Additionally, the spline may include notches similar to notches 708, and an aperture offset from a rotational axis of the elongate body of the spline.

Figure 10:
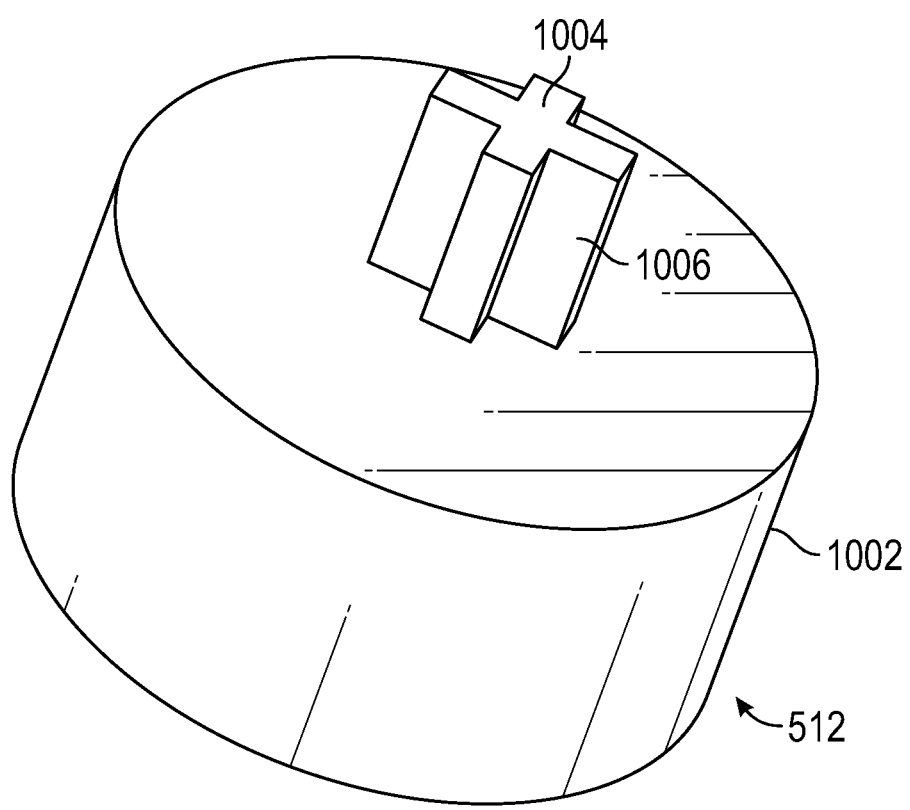
FIGS. 10 and 11 illustrate a perspective view of an alternate engagement mechanism between a coupler of the sterile adapter and a tool, according to some embodiments.
Figure 11:
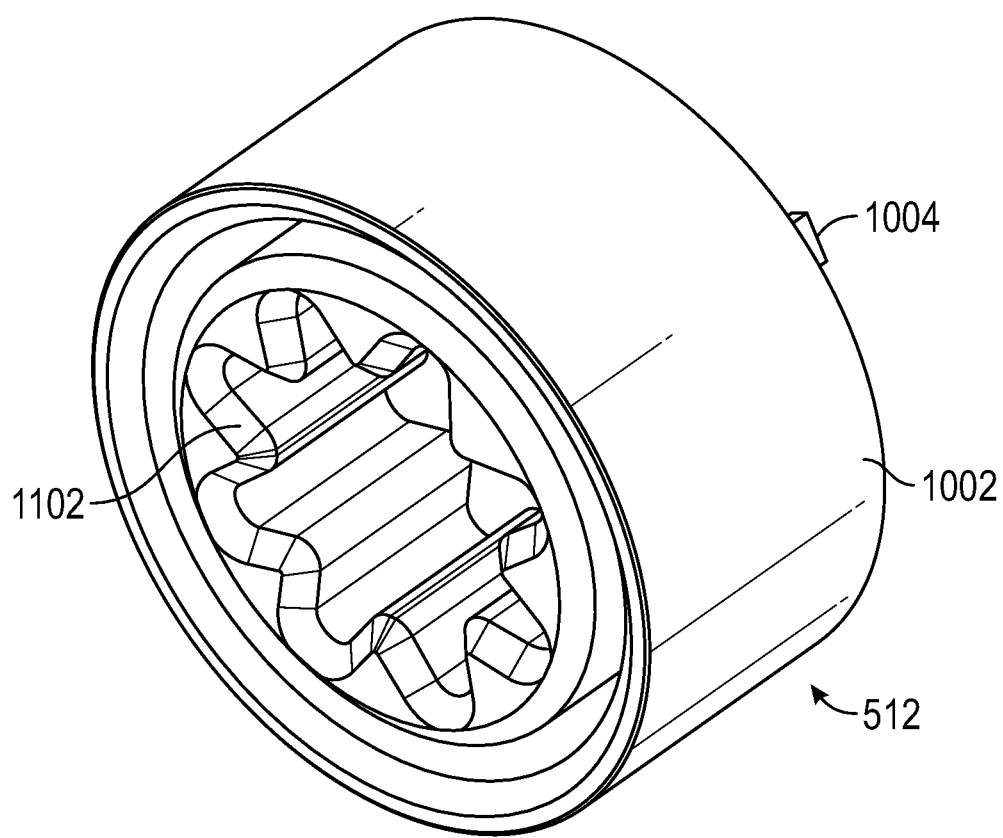

FIGS. 10-11 illustrate a perspective view of an alternate engagement mechanism between a coupler 512 of the sterile adapter 506 and a tool, according to some embodiments of the present disclosure. In some embodiments, the driveshaft coupler 512 includes a base 1002. On the tool side, the base 1002 may include an engagement component including a fixed alignment member 1004 having a plurality of notches or fins 1006. On the IDM side, the base 1002 may have slots 1102 complementary to the notches of the corresponding IDM base driveshaft. As with the embodiment illustrated in FIGS. 7-9, each coupler 512 is configured to rotate in a clockwise or counter-clockwise direction with the corresponding base driveshaft.

It will be appreciated that in the context of the present disclosure, the fixed alignment member 1004 can be fixed relative to the coupler 512 and may move with the coupler 512. For example, (the fixed alignment member 1004 may rotate about the rotational axis of the coupler 512 when the coupler 512 is rotated when engaged with the corresponding base driveshaft of the IDM during operation of the robotic system.

In some embodiments, the fixed alignment member 1004 may be integrally formed with the coupler 512. For example, the fixed alignment member 1004 is formed during the same process (e.g., molding) as the base 1002, rather than being a separate part that is fastened or otherwise attached to the base 1002.

When a tool is being coupled to the coupler 512, the fixed alignment member 1004 engages with a corresponding engagement component including a moveable alignment member provided at the tool driveshaft. The engagement of the fixed alignment member 1004 with the corresponding moveable alignment member permits engagement between the coupler 512 and the tool driveshaft. Engagement between the coupler 512 and the tool driveshaft is permitted only when the rotational positions of the coupler 512 and the tool driveshaft are aligned.

Based on the shape of the fixed alignment member 1004, there may be multiple rotational positions at which the coupler 512 and the tool driveshaft are aligned. For example, for the fixed alignment member 1004 having four (4) notches/fins 1006 placed with 2-fold rotational symmetry around the rotational axis of the coupler 512, engagement between the fixed alignment member 1004 and a correspondingly shaped moveable alignment member on the tool driveshaft may possible at every 180° of rotation about the rotational axis. For example, for the embodiment illustrated in FIG. 10, the fins 1006 are arranged with a longer set of fins along one axis than a second set of fins along a perpendicular axis, such that the engagement between the coupler 512 and the tool driveshaft is possible at 2 rotational positions.

While FIG. 10 shows the fixed alignment member 1004 having four notches/fins 1006, one of ordinary skill in the art will appreciate that the fixed alignment member 1004 may have any number of notches or fins 1006. One of ordinary skill in the art will further appreciate that the number and the rotational symmetry of the fins/notches provided to the fixed alignment member determines the number of rotational positions at which the fixed alignment member can engage with a corresponding shaped moveable alignment member.

For example, in some embodiments, the fixed alignment member may have 4 notches/fins arranged in a 4-fold symmetry (rather than the 2-fold symmetry shown in FIG. 11) by providing four notches/fins of the same size and shape arranged every 90 degrees. Such configuration results in four, rather than two rotational positions at which the coupler 512 can be aligned and engaged with the tool driveshaft having correspondingly shaped moveable alignment member. Embodiments with four notches/fins having shapes other than a cross or a plus are contemplated within the scope of the present disclosure. Likewise, embodiments with fixed alignment members having two, three or more than four notches/fins are contemplated within the scope of the present disclosure.

E. Instruments for Performing Medical Procedures

Figure 12:
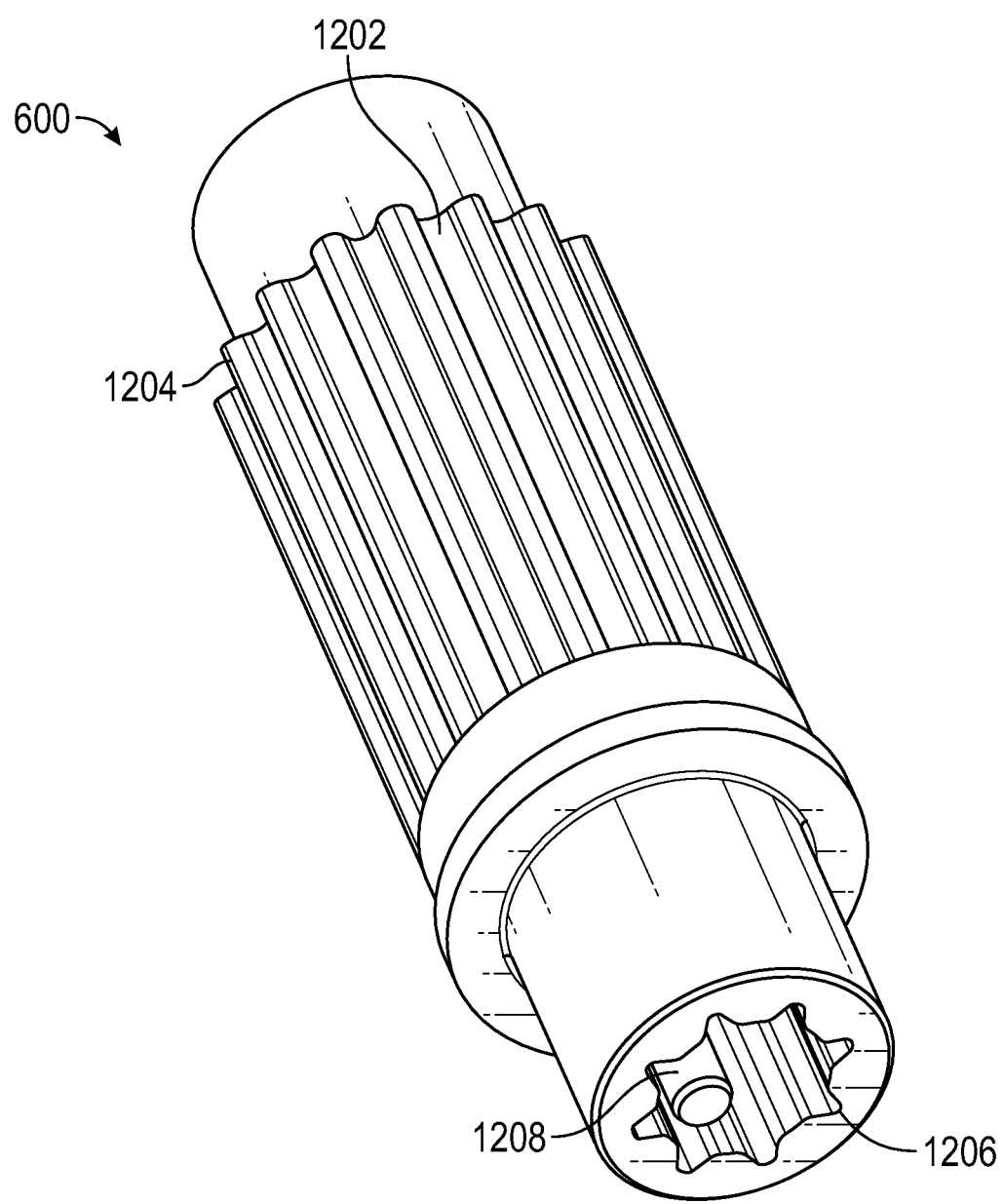
FIG. 12 illustrates a perspective view of a tool driveshaft, according to some embodiments.

FIG. 12 illustrates a perspective view of a tool driveshaft 600 in according to some embodiments of the present disclosure. In some embodiments, the tool driveshaft 600 includes a cylindrical body 1202 having a plurality of notches 1204 on one side, and a plurality of slots 1206 on another side. The notches 1204 engage with various drive mechanisms, such as gears and pulleys, of the tool so as to move or operate the end-effectors of the tool. The plurality of slots 1206 are complementary to the notches of a corresponding IDM base driveshaft or those of a corresponding driveshaft coupler of a sterile adapter. The tool driveshaft 600 further includes an engagement component including a fixed alignment member 1208.

As described herein, the fixed alignment member 1208 can be "fixed" relative to the tool driveshaft 600, and may move with the tool driveshaft 600 during operation. For example, the fixed alignment member 1208 may revolve around the rotational axis of the tool driveshaft 600 when the tool driveshaft 600 rotates.

In some embodiments, the fixed alignment member 1208, is positioned to be offset from the rotational axis of the tool driveshaft 600. The fixed alignment member 1208 is shaped to be received into an aperture of a moveable alignment member of an engagement component of the corresponding base driveshaft of an IDM or the corresponding driveshaft coupler of a sterile adapter when the rotational position of the base driveshaft or the driveshaft coupler is aligned with the rotational position of the tool driveshaft.

The position of the fixed alignment member 1208 can be established to ensure alignment of the notches of the base driveshaft or driveshaft coupler with corresponding slots 1206 of the tool driveshaft 600. Thus, when the fixed alignment member 1208 is received in the corresponding aperture of the engagement component of base driveshaft or driveshaft coupler, the base driveshaft or the driveshaft coupler is fully engaged with the tool driveshaft 600. Such complete engagement between the base driveshaft or the driveshaft coupler and the tool driveshaft 600 can ensure that there is no relative rotational movement between the base driveshaft or the driveshaft coupler and the tool driveshaft 600 during operation of the robotic system. The motion or torque from the base driveshaft or the driveshaft coupler is, thus, transferred to the tool driveshaft 600 without latency.

In some embodiments, the tool driveshaft 600 illustrated in FIG. 12 is configured to engage with the driveshaft coupler 512 illustrated in FIGS. 7-9. In such embodiments, the tool driveshaft 600 engages with the driveshaft coupler 512 only at a position at which the fixed alignment member 1208 is received in the aperture 708. Thus, because of the offset positioning of the fixed alignment member 1208, engagement between the tool driveshaft 600 and the driveshaft coupler 512 is possible only at one rotational position.

The rotational position of the tool driveshaft 600 at the time of coupling the tool to the robotic system can be determined by determining the rotational position of the base driveshaft at which the fixed alignment member 1208 is received in the aperture of the moveable alignment member associated with the base driveshaft. This rotational position of the base driveshaft may be termed as the "zero-position" for the corresponding tool driveshaft. By determining the "zero-position" of all the tool driveshafts, the position of the end-effector of the tool at the time of the tool is coupled to the robotic system can be determined. Knowing the "zero-position" enables the user to determine the magnitude and direction of an initial movement of the end-effector during the procedure.

Those of ordinary skill in the art will appreciate that while a single fixed alignment member 1208 positioned to be offset from the corresponding rotational axis is described and illustrated herein, the engagement component of the tool driveshaft is not restricted to such embodiments.

For example, in some embodiments, the fixed alignment member with a non-circular shape may be positioned along the rotational axis of the tool driveshaft 600 such that the corresponding aperture in the moveable alignment member can engage with the fixed alignment member at a single rotational position. Examples of such fixed alignment members may include protrusions having a T-shaped structure, an I-shaped structure with differently sized horizontal bars, an L-shaped structure, or a bar positioned asymmetrically relative to the rotational axis of the tool driveshaft 600.

Likewise, in some embodiments, the fixed alignment member may be shaped such that there are two rotational positions of engagement. For example, a protrusion shaped like a rectangular base and symmetrically positioned along the rotational axis of the coupler 512 may be received in a correspondingly shaped aperture at two different rotational positions. Other shapes (such as an equilateral triangle, square, a plus, a cross, a regular hexagon, a pentalobe, etc.) of the protrusion, allowing for more than two rotational positions of engagement between the tool and the base driveshaft or driveshaft coupler are also contemplated in the scope of the present disclosure.

Thus, while the embodiment illustrated in FIG. 12 shows a cylindrical protrusion as the fixed alignment member 1208 that can be receive in a circular aperture, the fixed alignment member 1208 may have the cross-sectional shape of a regular or irregular, polygon which may or may not be a convex polygon. Thus, the fixed alignment member may have any cross-sectional shape such as, for example, triangle, quadrangle, pentagon, hexagon, pentalobe, I-shaped, cross-shaped, or plus-shaped.

Figure 13:
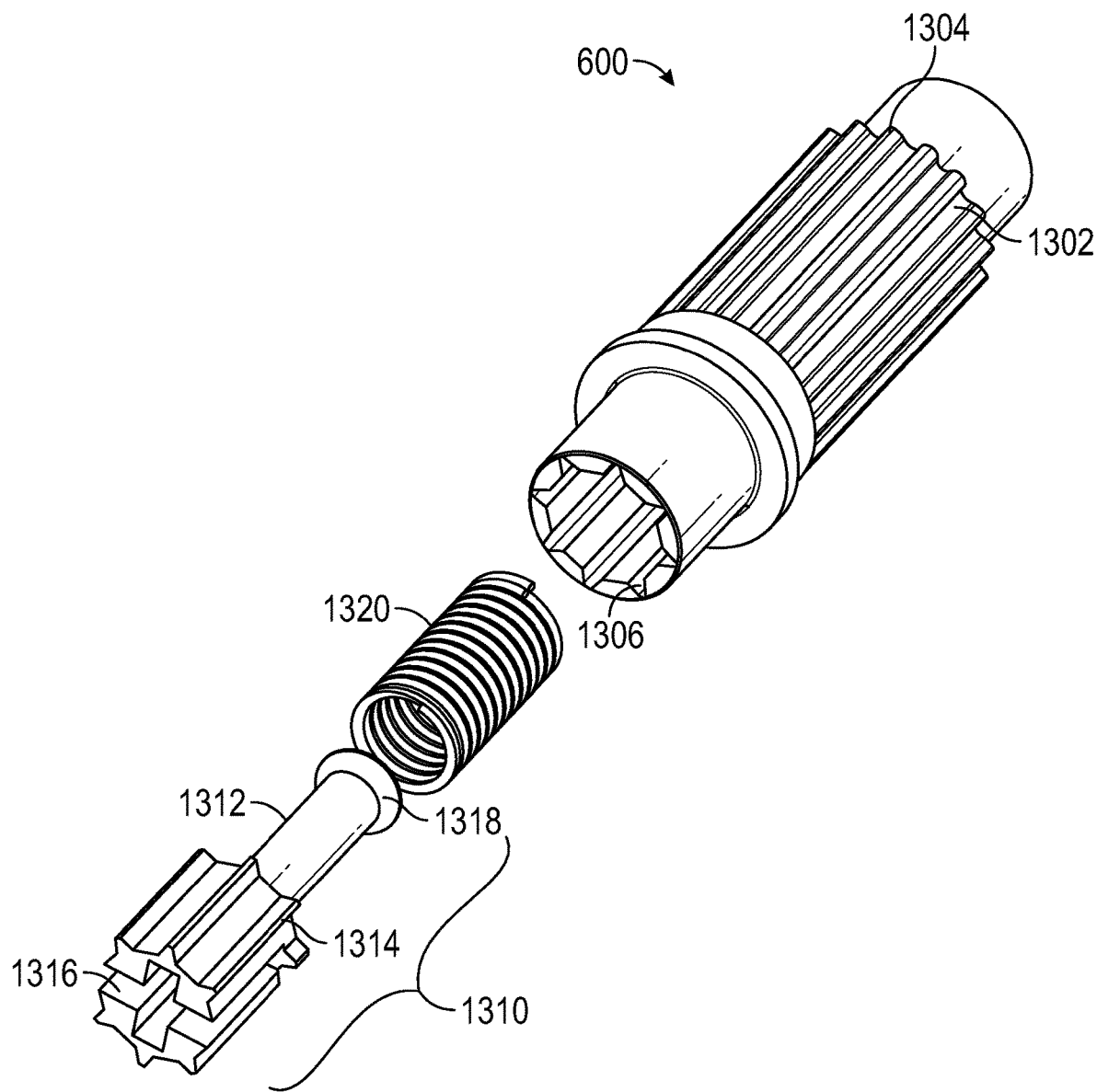
FIG. 13 illustrates an exploded perspective view of a tool driveshaft having an alternate engagement mechanism, according to some embodiments.
Figure 14:
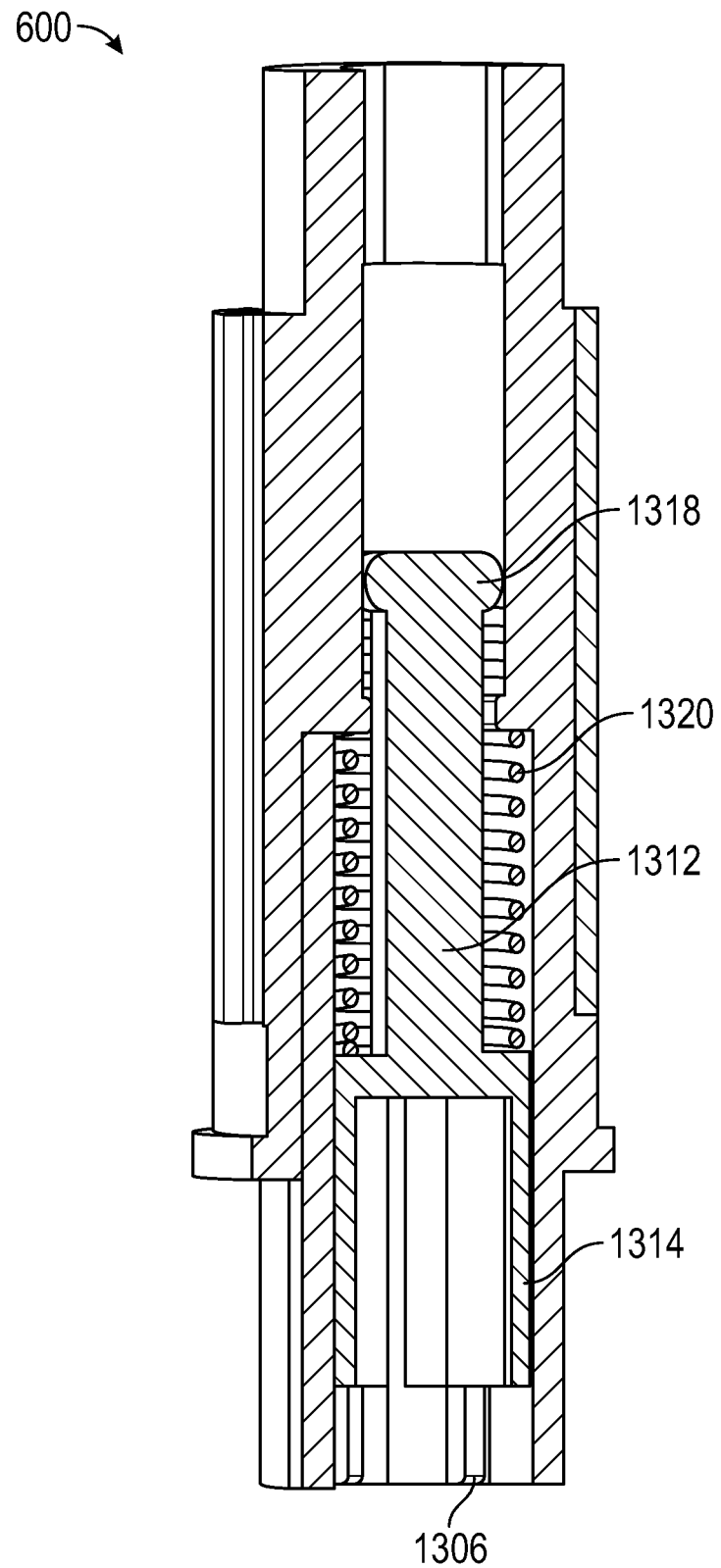
FIG. 14 illustrates a cross-section view of the tool driveshaft having the alternate engagement mechanism illustrated in FIG. 13.

FIG. 13 illustrates an exploded perspective view of a tool driveshaft 600 having an alternate engagement mechanism according to some embodiments of the present disclosure. FIG. 14 illustrates a cross-section view of the tool driveshaft 600 having the alternate engagement mechanism illustrated in FIG. 13. In some embodiments, the tool driveshaft 600 illustrated in FIGS. 13 and 14 is configured to engage with the driveshaft coupler 512 illustrated in FIGS. 10-11.

In the embodiment illustrated in FIGS. 13 and 14, the tool driveshaft 600 includes a cylindrical body 1302 having a plurality of notches 1304 on one side, and a plurality of slots 1306 on the other side. The notches 1304 engage with various drive mechanisms, e.g., gears or pulleys, of the tool so as to move or operate the end-effectors of the tool. The tool driveshaft 600 further includes an engagement component including a moveable alignment member 1310. The plurality of slots 1306 are complementary to notches provided on the moveable alignment 1310 such that relative rotational movement between the moveable alignment member 1310 and the tool driveshaft 600 is not possible. For example, the tool driveshaft 600 rotates with the moveable alignment member 1310.

Further, while the relative rotational movement between the moveable alignment member 1310 and the tool driveshaft 600 is constrained, the moveable alignment member 1310 is capable of translational movement relatively to the tool driveshaft 600.

Moreover, once the tool driveshaft 600 is coupled to the robotic system, the moveable alignment member 1310 reduces or prevents relative rotational movement between the base driveshaft of the IDM (and the coupler driveshaft of the sterile adapter) and the tool driveshaft, as is described herein.

The moveable alignment member 1310 may include a shaft 1312, a plurality of notches 1314 extending from a first end of the shaft 1312 and a plurality of slots 1316 at the first end of the shaft 1312. The shaft 1312 is shaped to allow the moveable alignment 1310 to translate in a cavity along the rotational axis of the tool driveshaft 600. The plurality of notches 1314 are structured to engage with the plurality of slots 1306 so as to reduce or prevent relative rotational movement between the moveable alignment member 1310 and the tool driveshaft 600. The plurality of slots 1316 are configured to receive correspondingly shaped fixed alignment member provided at a base driveshaft of an IDM or a driveshaft coupler of a sterile adapter.

The engagement component can further include a biasing member 1320, such as a coil spring. The biasing member 1320 can bias the moveable alignment member 1310 to an extended position in which it may engage with a corresponding fixed alignment member of the base driveshaft of the IDM or the driveshaft coupler of the sterile adapter. FIGS. 13 and 14 illustrate an embodiment in which a tool has a tool driveshaft 600 that is coupled to the robotic system. In such an embodiment, the moveable alignment member 1310 can engage with a corresponding engagement component. For example, the moveable alignment member 1310 can engage with a fixed alignment member of a tool (e.g., as illustrated in FIGS. 10-11). The fixed alignment member can be disposed on the base driveshaft or the driveshaft coupler, which can permit engagement between the base driveshaft or the driveshaft coupler with the tool driveshaft 600.

Depending on the profile of the moveable alignment member 1310 (e.g., shape, number of notches), the engagement between the moveable alignment member 1310 and the corresponding fixed alignment member is possible only at certain rotational positions of the base driveshaft. At other positions, however, the notches of the fixed alignment member of the base driveshaft (or the driveshaft coupler) are not aligned with the plurality of slots 1316 of the fixed alignment member 1310. Such misalignment causes the fixed alignment member to push against an end of the moveable alignment member 1310, depressing (or retracting) of the moveable alignment member 1310 into the tool driveshaft 600 and compressing the spring 1320.

When the rotational position of the base driveshaft (and the driveshaft coupler) aligns with that of the tool driveshaft 600, the notches of the fixed alignment member align with the slots 1316, causing the fixed alignment member to be received into the moveable alignment member 1310, thereby removing the force being exerted on the moveable alignment member 1310. The compressed spring 1320 then releases the stored energy, thereby urging the moveable alignment member 1310 in an extended position where it engages with the base driveshaft (or the driveshaft coupler).

In some embodiments, the moveable alignment member 1310 further includes a stub 1318 at an end opposite the end having the slots 1316. The stub 1318 reduces or prevents the spring 1320 from disengaging from the shaft 1312 of the moveable alignment member 1310.

Based on the shape and number of slots 1316 in the moveable alignment member 1310, there may be multiple rotational positions at which the tool driveshaft 600 aligns with the base driveshaft (or the driveshaft coupler). For example, for the moveable alignment member 1310 having four (4) slots 1316 placed with 2-fold rotational symmetry around the rotational axis of the tool driveshaft 600, engagement between the moveable alignment member 1310 and a correspondingly shaped fixed alignment member on the based driveshaft (or driveshaft coupler) may possible at every 90° of rotation about the rotational axis. For example, for the embodiment illustrated in FIGS. 13 and 14, the slots 1316 are arranged with a longer set of slots along one axis than a second set of slots along a perpendicular axis, such that the engagement between the tool driveshaft 600 and the base driveshaft (or the driveshaft coupler) is possible at 2 rotational positions.

While FIG. 13 shows the moveable alignment member 1310 having four slots 1316, one of ordinary skill in the art will appreciate that the moveable alignment member 1310 may have any number of slots 1316. One of ordinary skill in the art will further appreciate that the number and the rotational symmetry of the slots provided to the moveable alignment member will determine the number of rotational positions at which the moveable alignment member can engage with a corresponding shaped fixed alignment member.

For example, in some embodiments, the moveable alignment member may have four slots arranged in a 4-fold symmetry (rather than the 2-fold symmetry shown in FIG. 13) by providing a four slots of the same size and shape and arranged every 90 degrees. Such configuration results in four, rather than two rotational positions at which the tool driveshaft 600 can be aligned and engaged with the base driveshaft (or driveshaft coupler) having correspondingly shaped fixed alignment member.

Similarly, embodiments with four slots having shapes other than a cross or a plus are contemplated within the scope of the present disclosure. Likewise, embodiments with fixed alignment members having two, three or more than four notches/fins are contemplated within the scope of the present disclosure.

F. Method of Coupling a Medical Tool to a Medical Robotic System,

In addition to the various inventive aspects of the medical robotic system, the sterile adapter, and the tool disclosed herein, also described herein is a method of preparing a medical robotic system.

In some embodiments, in order to prepare to operate the robotic system, a tool can be being coupled to the IDM (or the sterile adapter), and a controller of the robotic system (e.g., the tool engagement module 125 of the controller 120) may independently rotate each base driveshaft until rotational position of the base driveshaft (and correspondingly of the driveshaft coupler) is aligned with the then present rotational position of the tool driveshaft. For example, each base driveshaft may be driven by a motor. The IDM may include a plurality of motors respectively coupled to the plurality of base driveshafts. Each motor can independently drive the corresponding base driveshaft to bring the base driveshaft into rotational alignment and engagement with the corresponding tool driveshaft.

When engagement components of each of the base driveshafts are engaged with the engagement components of each of the tool driveshafts, the corresponding base driveshaft and the tool driveshaft are coupled, thereby permitting transfer of torque and rotary motion between the base driveshaft and the tool driveshaft.

Optionally, during this process, the rotational positions of the tool driveshafts at which the engagement between the corresponding engagement components occurs can provide information about the then present position. For example, a sensing component such as an encoder and/or a torque sensor in which the IDM may be configured to detect information indicative of the rotational position at which engagement occurs.

For example, the rotational positions of the tool driveshafts can provide information about the zero-position of the end-effectors of the tool. As described herein, the determination of the zero-position assists the user in determining the magnitude and direction of the initial movement the user must make to safely perform the procedure using the tool.

The method for preparing a medical robotic system disclosed herein facilitates complete engagement of the driveshafts of the tool being coupled to the medical robotic system with the driveshafts of the IDM. The complete engagement between driveshafts reduces or prevents grinding of the driveshafts against each other, and also reduces or prevents relative rotational movement between the driveshafts while the driveshafts are engaged (i.e., while the tool is coupled to the robotic system). This reduces or prevents any lag or delay between a movement initiated by the user and the actual movement of the end effector of the tool once the tool is coupled.

Advantageously, by enabling the determination of the rotational positions of each of the driveshafts of the tool being coupled to the robotic system at the time of the coupling, the method also enables detection of the position of the end-effectors of the tool (i.e., the zero-position), allowing the user to determine the direction and magnitude of an initial movement of the end effectors when initiating the procedure. Such determination of initial position of the end-effectors of the tool may also reduce or prevent overdrive or underdrive of the end-effectors, thereby reducing the possibility of inadvertent damage to the tool.

G. Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A surgical robotic system comprising: an instrument device manipulator having a base driveshaft that defines a first rotational axis; a tool having a tool driveshaft that defines a second rotational axis, wherein rotational positions of the base driveshaft and the tool driveshaft are alignable for permitting engagement between the base driveshaft and the tool driveshaft for transferring torque and rotary motion to the tool driveshaft; and a force transfer mechanism having a moveable alignment member and a fixed alignment member. The moveable alignment member has (i) a disengaged position in which the moveable alignment member is out of engagement with the fixed alignment member, thereby preventing engagement between the base driveshaft and the tool driveshaft and permitting rotation of the base driveshaft relative to the tool driveshaft, and (ii) an engaged position in which the rotational positions of the base driveshaft and the tool driveshaft are aligned with each other and the moveable alignment member is extended and in engagement with the fixed alignment member, thereby permitting engagement between the base driveshaft and the tool driveshaft and permitting transfer of torque and rotary motion from the base driveshaft to the tool driveshaft.

Clause 2. The surgical robotic system of Clause 1, wherein in the disengaged position, the rotational positions of the base driveshaft and the tool driveshaft are not aligned.

Clause 3. The surgical robotic system of any of the preceding Clauses, wherein in the engaged position, the base driveshaft and the tool driveshaft are rotationally aligned.

Clause 4. The surgical robotic system of any of the preceding Clauses, wherein the moveable alignment member is provided on a sterile adapter coupled to the instrument device manipulator, the moveable alignment member being moveable relative to the base driveshaft.

Clause 5. The surgical robotic system of any of the preceding Clauses, wherein fixed alignment member is provided on a sterile adapter coupled to the instrument device manipulator, the fixed alignment member being fixed relative to the base driveshaft.

Clause 6. The surgical robotic system of any of the preceding Clauses, wherein the moveable alignment member is depressible into the instrument device manipulator, a sterile adapter coupled to the instrument device manipulator, or the tool and biased towards an extended position.

Clause 7. The surgical robotic system of any of the preceding Clauses, wherein the moveable alignment member comprises an aperture offset from the first rotational axis, the aperture being configured to receive the fixed alignment member.

Clause 8. The surgical robotic system of Clause 7, wherein the aperture is configured to receive the fixed alignment member when the rotational positions of the base driveshaft and the tool driveshaft are aligned and the moveable and fixed alignment members are aligned.

Clause 9. The surgical robotic system of any of the preceding Clauses, wherein the moveable alignment member further comprises a spline.

Clause 10. The surgical robotic system of Clause 9, wherein the spline has an aperture offset from the first rotational axis or the second rotational axis.

Clause 11. The surgical robotic system of Clause 9, wherein the spline comprises an elongate body having a cross-sectional shape selected from the group consisting of: a circle, a quadrangle, a convex polygon, a non-convex polygon, or any combination thereof.

Clause 12. The surgical robotic system of Clause 9, wherein the spline comprises cylindrical body and the aperture comprises a circular hole.

Clause 13. The surgical robotic system of any of the preceding Clauses, wherein the force transfer mechanism further comprises a spring for urging the moveable member to an extended position.

Clause 14. The surgical robotic system of any of the preceding Clauses, wherein the fixed member comprises an axially extending protrusion offset from the first rotational axis or the second rotational axis.

Clause 15. The surgical robotic system of any of the preceding Clauses, further comprising a controller configured to cause the base driveshaft to be rotated relative to the tool driveshaft to permit the moveable alignment member to move to the extended position to be coupled with the fixed alignment member, thereby permitting the transfer of force between the base driveshaft and the tool driveshaft.

Clause 16. The surgical robotic system of Clause 15, wherein the controller is further configured to determine a zero-position of the tool driveshaft based on a rotational position of the base driveshaft when the base driveshaft first engages with the tool driveshaft.

Clause 17. The surgical robotic system of any one of preceding Clauses, further comprising a sterile adapter between the instrument device manipulator and the tool, and a spring in the sterile adapter configured to bias the moveable alignment member to an extended position.

Clause 18. A method of coupling a surgical tool to a surgical robot, the method comprising: rotating a base driveshaft of an instrument device manipulator (instrument device manipulator) of the surgical robot relative to a tool driveshaft of the surgical tool to be coupled to the instrument device manipulator; permitting a moveable alignment member of a force transfer mechanism to be in a retracted position when rotational positions of the base driveshaft and the tool driveshaft are not aligned for reducing or preventing transfer of force between the base driveshaft and the tool driveshaft; and permitting the moveable alignment member to move to an extended position and be coupled with a fixed alignment member of the force transfer mechanism when the rotational positions of the base driveshaft and the tool driveshaft are aligned, thereby permitting engagement between the base driveshaft and the tool driveshaft and transfer of force between the base driveshaft and the tool driveshaft.

Clause 19. The method of Clause 18, wherein the fixed member comprises an axially extending protrusion offset from the rotational axis of the base driveshaft or the tool driveshaft.

Clause 20. The method of any of Clauses 18 to 19, wherein the moveable alignment member further comprises a spline coupled to a biasing member, wherein permitting the moveable alignment member to be in the retracted position comprises storing energy in the biasing member by depressing the moveable alignment member, and permitting the moveable alignment member to be in the extended position comprises releasing energy from the biasing member by urging the moveable member to an extended position.

Clause 21. The method of any of Clauses 18 to 20, wherein the moveable alignment member further comprises a spline having an aperture offset from the rotational axis of the base driveshaft or the tool driveshaft.

Clause 22. The method of any of Clauses 20 or 21, wherein the spline comprises an elongate body having a cross-sectional shape selected from the group consisting of: a circle, a quadrangle, a convex polygon, a non-convex polygon, and any combination thereof.

Clause 23. The method of any of Clauses 18 to 22, further comprising determining a zero-position of the tool driveshaft based on a rotational position of the base driveshaft when the base driveshaft first engages with the tool driveshaft.

Clause 24. The method of any of Clauses 18 to 23, wherein a relative rotational movement between the base driveshaft and the tool driveshaft is reduced or prevented, upon coupling of the moveable alignment member with the fixed alignment member.

Clause 25. A sterile adapter for a surgical robot, comprising: a body; and a coupler configured to engage with a base driveshaft of an instrument device manipulator (instrument device manipulator) of the surgical robot on a first side, engage with a tool driveshaft of a tool being coupled to the surgical robot on a second side opposite the first side. The coupler comprises a first engagement part configured to engage with a second engagement part provided at the tool driveshaft when a rotational position of the coupler is aligned with a rotational position of the tool driveshaft, thereby permitting transfer of rotary motion from the base driveshaft to the tool driveshaft. The coupler is configured to reduce or prevent transfer of rotary motion from the base driveshaft to the tool driveshaft when the first engagement part is not in engagement with the second engagement part.

Clause 26. The sterile adapter of Clause 25, wherein the first engagement part comprises a spring-loaded portion configured to retract into the body towards the first side when the rotational positions of the coupler and the tool driveshaft are not aligned.

Clause 27. The sterile adapter of Clause 26, wherein the first engagement part further comprises an aperture offset from a rotational axis of the coupler, the aperture being configured to receive a protrusion provided at the tool driveshaft when the rotational positions of the coupler and the tool driveshaft are aligned.

Clause 28. The sterile adapter of any of Clauses 25 to 27, wherein the first engagement part comprises a protrusion fixed relative to the coupler, the protrusion being configured to engage with a correspondingly shaped aperture provided in the tool driveshaft when the rotational positions of the coupler and the tool driveshaft are aligned.

Clause 29. A surgical robotic tool, comprising: a tool driveshaft having a rotational position alignable with a rotational position of a base driveshaft of an instrument device manipulator having a fixed alignment member; and a moveable alignment member configured to have: (i) a disengaged position in which the moveable alignment member is recessed and out of engagement with the fixed alignment member when the rotational positions of the base driveshaft and the tool driveshaft are not aligned for reducing or preventing transfer of motion between the base driveshaft and the tool driveshaft, and (ii) an engaged position in which the moveable alignment member extends into engagement with the fixed alignment member when the rotational positions of the base driveshaft and the tool driveshaft are aligned for permitting transfer of motion between the base driveshaft and the tool driveshaft.

Clause 30. The surgical robotic tool of Clause 29, wherein the moveable alignment member is configured to reduce or prevent, when in the engaged position, relative rotational movement between the base driveshaft and the tool driveshaft.

Clause 31. The surgical robotic tool of any of Clauses 29 to 30, wherein the moveable alignment member spaced apart from the rotational axis of the tool driveshaft.

Clause 32. The surgical robotic tool of any of Clauses 29 to 31, wherein the moveable alignment member comprises a spline coupled to a biasing member.

Clause 33. A surgical robotic system, the system comprising a base driveshaft having a first rotational axis and a first engagement interface and a tool driveshaft having a second rotational axis and a second engagement interface, wherein the base driveshaft and the tool driveshaft move to an engaged position for transferring force to the tool driveshaft when the first and second rotational axes are coaxially aligned with respect to each other and the first and second engagement interfaces are rotationally aligned with respect to each other.

Clause 34. The surgical robotic system of Clause 33, wherein the first engagement interface comprises an aperture configured to receive the second engagement interface.

Clause 35. The surgical robotic system of any of Clauses 33 to 34, wherein the first and second engagement interfaces are offset from the first and second rotational axes.

Clause 36. The surgical robotic system of any of Clauses 33 to 35, wherein, the first and second engagement interfaces are configured to reduce or prevent, upon rotational alignment of the first and second engagement interface, relative rotational motion between the base driveshaft and the tool driveshaft.

Clause 37. The surgical robotic system of any of Clauses 33 to 36, further comprising an instrument device manipulator optionally coupled to a sterile adapter, and a tool, wherein the instrument device manipulator or the sterile adapter coupled to the instrument device manipulator comprises the first engagement interface and the tool comprises the second engagement interface.

Clause 38. A surgical robotic system, the system comprising: a base driveshaft that defines a first rotational axis and has a first member; a tool having (i) a tool driveshaft that defines a second rotational axis and (ii) an engagement interface having a second member, the second member being offset from the second rotational axis. The base driveshaft is engageable with the tool driveshaft upon alignment rotational positions of the tool driveshaft and the base driveshaft for permitting engagement between the base driveshaft and the tool driveshaft for transferring rotary motion to the tool driveshaft.

Clause 39. A surgical robotic tool, comprising: a tool driveshaft having a rotational position alignable with a rotational position of a base driveshaft of an instrument device manipulator; and a fixed alignment member configured to engage a moveable alignment member of the instrument device manipulator when the rotational positions of the base driveshaft and the tool driveshaft are aligned for permitting transfer of motion between the base driveshaft and the tool driveshaft.

Clause 40. The surgical robotic tool of Clause 39, wherein in the fixed alignment member is configured to reduce or prevent, upon engagement with the moveable alignment member, relative rotational movement between the base driveshaft and the tool driveshaft.

Clause 41. The surgical robotic tool of Clause 40, wherein the fixed member comprises an axially extending protrusion offset from the rotational axis of the base driveshaft or the rotational axis of the tool driveshaft.

Clause 42. A surgical robotic tool comprising any of the features disclosed herein.

Clause 43. A robotic system comprising any of the features disclosed herein.

Clause 44. A method of operating or manufacturing a surgical robotic tool or robotic system comprising any of the features disclosed herein.

H. Further Considerations

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The singular forms "a," "an," and "the" include plural referents unless the context clearly dictates otherwise. Thus, for example, reference to "a plunger component" includes reference to one or more plunger components, and reference to "the magnet" includes reference to one or more magnets.

In one or more aspects, the terms "about," "substantially," and "approximately" may provide an industry-accepted tolerance for their corresponding terms and/or relativity between items, such as from less than one percent to five percent.

The term "subject" refers to a mammal that may benefit from the administration using a transdermal device or method of this disclosure. Examples of subjects include humans, and other animals such as horses, pigs, cattle, dogs, cats, rabbits, and aquatic mammals.

As used herein, the term "substantially" refers to the complete or nearly complete extent or degree of an action, characteristic, property, state, structure, item, or result.

It is to be understood that a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this disclosure belongs. Although any methods, devices and materials similar or equivalent to those described herein can be used in the practice or testing of the disclosure, representative methods, devices, and materials are described below.

The word "exemplary" is used herein to mean "serving as an example, instance, or illustration." Any embodiment described herein as "exemplary" is not necessarily to be construed as preferred or advantageous over some embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes some embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A surgical robotic system comprising:
   an instrument device manipulator having a base driveshaft that defines a first rotational axis;
   a tool having a tool driveshaft that defines a second rotational axis, wherein rotational positions of the base driveshaft and the tool driveshaft are alignable for permitting engagement between the base driveshaft and the tool driveshaft for transferring torque and rotary motion to the tool driveshaft; and
   a force transfer mechanism having a moveable alignment member and a fixed alignment member, the moveable alignment member having:
   (i) a disengaged position in which the moveable alignment member is out of engagement with the fixed alignment member, thereby preventing engagement between the base driveshaft and the tool driveshaft and permitting rotation of the base driveshaft relative to the tool driveshaft, and
   (ii) an engaged position in which the rotational positions of the base driveshaft and the tool driveshaft are aligned with each other and the moveable alignment member is extended and in engagement with the fixed alignment member, thereby permitting engagement between the base driveshaft and the tool driveshaft and permitting transfer of torque and rotary motion from the base driveshaft to the tool driveshaft.

2. The surgical robotic system of claim 1, wherein in the disengaged position, the rotational positions of the base driveshaft and the tool driveshaft are not aligned.

3. The surgical robotic system of claim 1, wherein in the engaged position, the base driveshaft and the tool driveshaft are rotationally aligned.

4. The surgical robotic system of claim 1, wherein the moveable alignment member is depressible into the instrument device manipulator, a sterile adapter coupled to the instrument device manipulator, or the tool and biased towards an extended position.

5. The surgical robotic system of claim 1, wherein the moveable alignment member comprises an aperture offset from the first rotational axis, the aperture being configured to receive the fixed alignment member.

6. The surgical robotic system of claim 1, wherein the moveable alignment member further comprises a spline.

7. The surgical robotic system of claim 1, wherein the force transfer mechanism further comprises a spring for urging the moveable member to an extended position.

8. The surgical robotic system of claim 1, wherein the fixed member comprises an axially extending protrusion offset from the first rotational axis or the second rotational axis.

9. The surgical robotic system of claim 1, further comprising a controller configured to cause the base driveshaft to be rotated a relative to the tool driveshaft to permit the moveable alignment member to move to the extended position to be coupled with the fixed alignment member, thereby permitting the transfer of force between the base driveshaft and the tool driveshaft.

10. The surgical robotic system of claim 9, wherein the controller is further configured to determine a zero-position of the tool driveshaft based on a rotational position of the base driveshaft when the base driveshaft first engages with the tool driveshaft.

11. The surgical robotic system of claim 1, further comprising:
    a sterile adapter between the instrument device manipulator and the tool; and a spring in the sterile adapter configured to bias the moveable alignment member to an extended position.

\* \* \* \* \*